United States Patent [19]
Clemente et al.

[11] Patent Number: 5,849,894
[45] Date of Patent: Dec. 15, 1998

[54] *RHODOSPIRILLUM RUBRUM* POLY-β-HYDROXYALKANOATE SYNTHASE

[75] Inventors: Thomas E. Clemente, Lincoln, Nebr.; Ganesh M. Kishore, Creve Coeur, Mo.; Timothy A. Mitsky, Maryland Heights, Mo.; David M. Stark, Chesterfield, Mo.

[73] Assignee: Monsanto Company, St. Louis, Mo.

[21] Appl. No.: 756,317

[22] Filed: Nov. 25, 1996

Related U.S. Application Data

[60] Provisional application No. 60/007,693, Nov. 29, 1995.
[51] Int. Cl.$^6$ .............................. C12N 9/00; C12N 15/00; C12N 1/20; C07H 21/04
[52] U.S. Cl. ..................... 536/23.2; 435/183; 435/320.1; 435/252.3; 935/22
[58] Field of Search ................................. 435/183, 252.3, 435/320.1, 410; 536/23.2; 935/22

[56] References Cited

U.S. PATENT DOCUMENTS

| | | | |
|---|---|---|---|
| 5,480,794 | 1/1996 | Peoples et al. | 435/232 |
| 5,502,273 | 3/1996 | Bright et al. | 800/205 |
| 5,610,041 | 3/1997 | Somerville et al. | 435/135 |
| 5,650,555 | 7/1997 | Somerville et al. | 800/205 |

OTHER PUBLICATIONS

Hustede et al. (1993) Characterization of the polyhydroxyalkanoate synthase gene locus of *Rhodobacter sphaerpodes*. Biotechnology Letters 15 (7): 709–714, Jul. 1993.

Timm et al. (1992) cloning and molecular analysis of the poly(3–hydroxyalkanoic acid) gene locus of *Pseudomonas aeruginosa* PAo1. Eur. J. Biochem. 209: 15–30, Jan. 1992.

Valentin et al. (1993) Cloning and characterization of the *Methylobacterium extorquens* polyhydroxyalkanoic–acid–synthase structural gene. Appl. Microbiol. Biotechnol. 39: 309–317, Mar. 1993.

Timm et al. (1994) A general method for identification of polyhydroxyalkanoic acid synthase genes from pseudomonads belonging to the rRNA homology group I. Appl. Microbiol. Biotechnol. 40: 669–675, Jun. 1994.

Schembri et al. (1994) Cloning and analysis of the polyhydroxyalkanoic acid synthase gene from an *Acinetobacter sp.*: Evidence that the gene is both plasmid and chromosomally located. FEMS Microbiology Letters 118: 145–152, Apr. 1994.

Gerngross et al. (1994) Overexpression and purification of the soluble polyhydroyalkanoate synthase from *Alcaligenes eutrophus*: Evidence for a required posttranslational modification for catalytic ativity. Biochemistry 33: 9311–9320, Aug. 1994.

*Primary Examiner*—Robert A. Wax
*Assistant Examiner*—Einar Stoce
*Attorney, Agent, or Firm*—Gary M. Bond; Arnold, White & Durkee

[57] ABSTRACT

Isolated DNA fragments encoding a *Rhodospirillum rubrum* (ATCC 25903) polyhydroxyalkanoate (PHA) synthase, or biologically functional equivalents thereof, are provided. Also provided is the deduced amino acid sequence of the *R. rubrum* PHA synthase. These molecules are useful in the production of PHAs in bacteria and plants.

10 Claims, 2 Drawing Sheets ns under PHA-accumulating conducive conditions (Brandl et al., supra, and Ulmer et al. (1994) Macromolecules 27:1675).

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1924 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 8..1921

( x i ) SEQUENCE DESCRIPTION: SEQ ID NO:1:

```
GAAGCCC ATG GGC TTC TTG GCC CTG GAT AAT CTT GAC GCC TAT TTC CGG        49
        Met Gly Phe Leu Ala Leu Asp Asn Leu Asp Ala Tyr Phe Arg
        1               5                   10

GCC GCG AGC CGC CCC ACC GGA TCG CCT GAC CGC CCT TGG TCA GGC CGA        97
Ala Ala Ser Arg Pro Thr Gly Ser Pro Asp Arg Pro Trp Ser Gly Arg
15              20                  25                  30

CCG TCC GAA CGG GAG GGA AAG ACC ATG ACC GAC ACG CGG GCC GAA GCC        145
Pro Ser Glu Arg Glu Gly Lys Thr Met Thr Asp Thr Arg Ala Glu Ala
                35                  40                  45

GAC TTA ACC GAG GTT TGG CGG GCC TGG GCG GCC TGG GGC GAG AAA AGC        193
Asp Leu Thr Glu Val Trp Arg Ala Trp Ala Ala Trp Gly Glu Lys Ser
            50                  55                  60

CGG ACG ATG TGG GCA ACG GCC CTG GGC GGC GCG GCG CCC CCT TCT TCC        241
Arg Thr Met Trp Ala Thr Ala Leu Gly Gly Ala Ala Pro Pro Ser Ser
        65                  70                  75

CCA TCC CCC TCG GGG CCC GAC CCG GCC GTT GGG GGC GGC CCG GCC GTC        289
Pro Ser Pro Ser Gly Pro Asp Pro Ala Val Gly Gly Gly Pro Ala Val
    80                  85                  90

GGG GGC GAC GCG GCG CGG GCC TTC CTT GAG GGG GTT TTG CGC CCT TCC        337
Gly Gly Asp Ala Ala Arg Ala Phe Leu Glu Gly Val Leu Arg Pro Ser
95              100                 105                 110

CAA CCC GTT CTG GAC GCC CAG GCG GCC TGG GCC CGC GAT ATC GCG GCG        385
Gln Pro Val Leu Asp Ala Gln Ala Ala Trp Ala Arg Asp Ile Ala Ala
                115                 120                 125

CTG TGT CAG GCC GCC GCT AAA CGG CTG CGG GGC GAA GAG GCG GCG CCG        433
Leu Cys Gln Ala Ala Ala Lys Arg Leu Arg Gly Glu Glu Ala Ala Pro
            130                 135                 140

GTG ATC GAA CCG GCG GGC GAT GAC AAC CGC TTC AAA GAT GAC GCC TGG        481
Val Ile Glu Pro Ala Gly Asp Asp Asn Arg Phe Lys Asp Asp Ala Trp
        145                 150                 155

ACC AAG GAT CCG CTG TTT GAC ACC CTG AAG CAG GGC TAT CTG CTG ACC        529
Thr Lys Asp Pro Leu Phe Asp Thr Leu Lys Gln Gly Tyr Leu Leu Thr
    160                 165                 170
```

| | | | | | | | | | | | | | | | | |
|---|---|---|---|---|---|---|---|---|---|---|---|---|---|---|---|---|
| GCC | CGG | CTG | GTC | GCC | ACC | ACC | TTG | GAA | AAC | AGC | GGC | GGC | GAC | CCG | GCC | 577 |
| Ala | Arg | Leu | Val | Ala | Thr | Thr | Leu | Glu | Asn | Ser | Gly | Gly | Asp | Pro | Ala | |
| 175 | | | | 180 | | | | | 185 | | | | | 190 | | |
| TGC | CGC | CAG | CGC | CTC | GCC | TTT | TAT | GGG | CGT | CAG | GTG | GTC | GAC | GCC | CTC | 625 |
| Cys | Arg | Gln | Arg | Leu | Ala | Phe | Tyr | Gly | Arg | Gln | Val | Val | Asp | Ala | Leu | |
| | | | | 195 | | | | | 200 | | | | | 205 | | |
| GCC | CCG | ACC | AAT | TTC | GCC | GCC | ACC | AAT | CCG | CTG | GTT | CGG | CGA | ACC | GCC | 673 |
| Ala | Pro | Thr | Asn | Phe | Ala | Ala | Thr | Asn | Pro | Leu | Val | Arg | Arg | Thr | Ala | |
| | | | 210 | | | | | 215 | | | | | 220 | | | |
| CTA | GAA | AGC | GGC | GGC | AAA | AGC | CTG | TTG | AAC | GGG | CTG | GAA | AAT | CTG | TTG | 721 |
| Leu | Glu | Ser | Gly | Gly | Lys | Ser | Leu | Leu | Asn | Gly | Leu | Glu | Asn | Leu | Leu | |
| | | 225 | | | | | 230 | | | | | 235 | | | | |
| CGC | GAC | CTG | GAA | CGC | GGC | GGC | CGG | CTG | CGC | CCG | ACG | ATG | AGC | GAT | | 769 |
| Arg | Asp | Leu | Glu | Arg | Gly | Gly | Arg | Leu | Arg | Pro | Thr | Met | Ser | Asp | | |
| | 240 | | | | | 245 | | | | | 250 | | | | | |
| GAA | ACC | GCC | TTC | GAG | GTT | GGT | CGC | ACC | CTG | GCC | ATG | ACG | CCG | GGC | AAG | 817 |
| Glu | Thr | Ala | Phe | Glu | Val | Gly | Arg | Thr | Leu | Ala | Met | Thr | Pro | Gly | Lys | |
| 255 | | | | | 260 | | | | | 265 | | | | | 270 | |
| GTG | GTC | TTT | CAA | AAC | GCC | CTG | ATG | CAG | TTG | ATC | TTA | TAT | GCG | CCG | ACC | 865 |
| Val | Val | Phe | Gln | Asn | Ala | Leu | Met | Gln | Leu | Ile | Leu | Tyr | Ala | Pro | Thr | |
| | | | | 275 | | | | | 280 | | | | | 285 | | |
| ACG | CCG | AAG | GTC | CAC | AAA | CGG | CCC | TTG | CTG | GTG | GTG | CCG | CCG | TGG | ATC | 913 |
| Thr | Pro | Lys | Val | His | Lys | Arg | Pro | Leu | Leu | Val | Val | Pro | Pro | Trp | Ile | |
| | | | 290 | | | | | 295 | | | | | 300 | | | |
| AAT | AAA | TTC | TAC | ATC | CTG | GAT | CTG | ACG | GAA | AAG | AAC | TCG | CTG | ATC | AAA | 961 |
| Asn | Lys | Phe | Tyr | Ile | Leu | Asp | Leu | Thr | Glu | Lys | Asn | Ser | Leu | Ile | Lys | |
| | | 305 | | | | | 310 | | | | | 315 | | | | |
| TAC | ATG | GTC | GAT | CAG | GGC | TTC | AGC | GTG | TTC | GTC | ATC | TCC | TGG | GTC | AAC | 1009 |
| Tyr | Met | Val | Asp | Gln | Gly | Phe | Ser | Val | Phe | Val | Ile | Ser | Trp | Val | Asn | |
| | 320 | | | | | 325 | | | | | 330 | | | | | |
| CCC | GAT | GCC | GGC | TTG | GCG | GAA | ACA | CGC | TTC | GAG | GAT | TAC | CTC | AGC | CAG | 1057 |
| Pro | Asp | Ala | Gly | Leu | Ala | Glu | Thr | Arg | Phe | Glu | Asp | Tyr | Leu | Ser | Gln | |
| 335 | | | | | 340 | | | | | 345 | | | | | 350 | |
| GGG | CCG | CTG | GCC | GCC | ATG | GAG | GTG | ATG | ACC | GAG | ATC | ACC | GGC | CAG | CGC | 1105 |
| Gly | Pro | Leu | Ala | Ala | Met | Glu | Val | Met | Thr | Glu | Ile | Thr | Gly | Gln | Arg | |
| | | | | 355 | | | | | 360 | | | | | 365 | | |
| GCT | CTC | GGA | CTG | GTC | GGC | TAT | TGC | ATC | GGC | GGC | ACC | CTG | ACC | GCC | TGC | 1153 |
| Ala | Leu | Gly | Leu | Val | Gly | Tyr | Cys | Ile | Gly | Gly | Thr | Leu | Thr | Ala | Cys | |
| | | | 370 | | | | | 375 | | | | | 380 | | | |
| ACC | CTG | GCG | GTA | CTG | GCG | GCG | CGA | CGG | GAC | CAT | CGG | GTG | AAA | TCG | GCC | 1201 |
| Thr | Leu | Ala | Val | Leu | Ala | Ala | Arg | Arg | Asp | His | Arg | Val | Lys | Ser | Ala | |
| | | 385 | | | | | 390 | | | | | 395 | | | | |
| ACC | CTG | CTT | ACT | ACC | CTG | GTC | GAT | TTT | TCC | GAG | CCG | GGC | GAG | TTG | GGC | 1249 |
| Thr | Leu | Leu | Thr | Thr | Leu | Val | Asp | Phe | Ser | Glu | Pro | Gly | Glu | Leu | Gly | |
| | | 400 | | | | | 405 | | | | | 410 | | | | |
| GTT | TTC | ATC | GAC | CCG | CCC | CTG | CTT | GAC | GCC | CTT | GAC | GAC | CAG | ATG | GCC | 1297 |
| Val | Phe | Ile | Asp | Pro | Pro | Leu | Leu | Asp | Ala | Leu | Asp | Asp | Gln | Met | Ala | |
| 415 | | | | | 420 | | | | | 425 | | | | | 430 | |
| CGC | GAC | GGC | GGG | CTT | GAC | GGC | GAC | CTC | TTG | TCG | ATG | GCC | TTC | AAC | ATG | 1345 |
| Arg | Asp | Gly | Gly | Leu | Asp | Gly | Asp | Leu | Leu | Ser | Met | Ala | Phe | Asn | Met | |
| | | | | 435 | | | | | 440 | | | | | 445 | | |
| CTG | CGC | GAC | AAC | GAC | CTG | ATC | TGG | TCG | GTC | TTC | ATC | AAC | AAC | TAC | CTG | 1393 |
| Leu | Arg | Asp | Asn | Asp | Leu | Ile | Trp | Ser | Val | Phe | Ile | Asn | Asn | Tyr | Leu | |
| | | | 450 | | | | | 455 | | | | | 460 | | | |
| CTG | GGC | AAG | ACC | CCC | GCC | GCC | TTC | GAT | CTG | CTC | TAT | TGG | AAC | GGC | GAT | 1441 |
| Leu | Gly | Lys | Thr | Pro | Ala | Ala | Phe | Asp | Leu | Leu | Tyr | Trp | Asn | Gly | Asp | |
| | | 465 | | | | | 470 | | | | | 475 | | | | |
| TCA | ACG | CGG | ATG | CCC | GCC | GCC | ATG | CAG | CGT | TAT | TAC | CTG | CGC | GAG | ATG | 1489 |
| Ser | Thr | Arg | Met | Pro | Ala | Ala | Met | Gln | Arg | Tyr | Tyr | Leu | Arg | Glu | Met | |
| | 480 | | | | | 485 | | | | | 490 | | | | | |

```
TAC  CAG  AAG  AAC  AAG  CTC  GTC  CAG  CCC  GGC  GGT  CTG  ACC  GTG  CTT  GGC    1537
Tyr  Gln  Lys  Asn  Lys  Leu  Val  Gln  Pro  Gly  Gly  Leu  Thr  Val  Leu  Gly
495                      500                 505                      510

CAT  GCC  CTC  GAC  CTG  CGG  CGC  ATT  CGC  ACC  CCG  GTT  TAT  CTT  CTG  TCG    1585
His  Ala  Leu  Asp  Leu  Arg  Arg  Ile  Arg  Thr  Pro  Val  Tyr  Leu  Leu  Ser
               515                      520                      525

GCC  CGC  GAC  GAT  CAC  ATC  GCG  CCG  TGG  ACA  AGC  ACC  TTC  AAG  GCC  ACC    1633
Ala  Arg  Asp  Asp  His  Ile  Ala  Pro  Trp  Thr  Ser  Thr  Phe  Lys  Ala  Thr
               530                      535                 540

GGG  CTT  TAT  GGC  GGA  CCG  CTG  CGC  TTC  GTG  CTG  GCG  GGC  AGC  GGC  CAT    1681
Gly  Leu  Tyr  Gly  Gly  Pro  Leu  Arg  Phe  Val  Leu  Ala  Gly  Ser  Gly  His
               545                      550                 555

ATC  GCC  GGG  GTG  ATC  AAC  CCG  CCG  GCC  AAG  GCC  CGC  TAC  GGC  TAT  TGG    1729
Ile  Ala  Gly  Val  Ile  Asn  Pro  Pro  Ala  Lys  Ala  Arg  Tyr  Gly  Tyr  Trp
560                      565                 570

ACC  AAT  GCG  GAC  ACC  TCC  CTG  GAG  GCC  GAG  TCC  TGG  CTA  GAG  GGC  GCC    1777
Thr  Asn  Ala  Asp  Thr  Ser  Leu  Glu  Ala  Glu  Ser  Trp  Leu  Glu  Gly  Ala
575                      580                 585                      590

ACG  CCC  CAC  GGG  GGC  TCC  TGG  TGG  CCC  GAT  TGG  GCG  GCC  TGG  GCG  GCC    1825
Thr  Pro  His  Gly  Gly  Ser  Trp  Trp  Pro  Asp  Trp  Ala  Ala  Trp  Ala  Ala
               595                      600                 605

GGT  TAC  GCT  GGC  CCC  AAA  GTC  CCC  GCC  CGC  GAC  CCG  ACC  AAA  GCC  CCC    1873
Gly  Tyr  Ala  Gly  Pro  Lys  Val  Pro  Ala  Arg  Asp  Pro  Thr  Lys  Ala  Pro
               610                      615                 620

CGC  CCG  CCT  TTG  GAA  GAC  GCG  CCG  GGA  TCT  TAC  TTC  AAG  GTT  AGG  ATC    1921
Arg  Pro  Pro  Leu  Glu  Asp  Ala  Pro  Gly  Ser  Tyr  Phe  Lys  Val  Arg  Ile
               625                      630                 635

TAA                                                                                1924
```

( 2 ) INFORMATION FOR SEQ ID NO:2:

( i ) SEQUENCE CHARACTERISTICS:
        ( A ) LENGTH: 638 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met  Gly  Phe  Leu  Ala  Leu  Asp  Asn  Leu  Asp  Ala  Tyr  Phe  Arg  Ala  Ala
1                 5                      10                      15

Ser  Arg  Pro  Thr  Gly  Ser  Pro  Asp  Arg  Pro  Trp  Ser  Gly  Arg  Pro  Ser
               20                 25                      30

Glu  Arg  Glu  Gly  Lys  Thr  Met  Thr  Asp  Thr  Arg  Ala  Glu  Ala  Asp  Leu
               35                 40                      45

Thr  Glu  Val  Trp  Arg  Ala  Trp  Ala  Ala  Trp  Gly  Glu  Lys  Ser  Arg  Thr
          50                 55                      60

Met  Trp  Ala  Thr  Ala  Leu  Gly  Gly  Ala  Ala  Pro  Pro  Ser  Ser  Pro  Ser
65                 70                      75                           80

Pro  Ser  Gly  Pro  Asp  Pro  Ala  Val  Gly  Gly  Pro  Ala  Val  Gly  Gly
               85                 90                      95

Asp  Ala  Ala  Arg  Ala  Phe  Leu  Glu  Gly  Val  Leu  Arg  Pro  Ser  Gln  Pro
               100                105                     110

Val  Leu  Asp  Ala  Gln  Ala  Ala  Trp  Ala  Arg  Asp  Ile  Ala  Ala  Leu  Cys
               115                120                     125

Gln  Ala  Ala  Ala  Lys  Arg  Leu  Arg  Gly  Glu  Glu  Ala  Ala  Pro  Val  Ile
               130                135                     140

Glu  Pro  Ala  Gly  Asp  Asp  Asn  Arg  Phe  Lys  Asp  Asp  Ala  Trp  Thr  Lys
145                     150                     155                     160
```

```
Asp Pro Leu Phe Asp Thr Leu Lys Gln Gly Tyr Leu Leu Thr Ala Arg
            165             170              175
Leu Val Ala Thr Thr Leu Glu Asn Ser Gly Gly Asp Pro Ala Cys Arg
            180             185             190
Gln Arg Leu Ala Phe Tyr Gly Arg Gln Val Val Asp Leu Ala Pro
        195             200             205
Thr Asn Phe Ala Ala Thr Asn Pro Leu Val Arg Arg Thr Ala Leu Glu
    210             215             220
Ser Gly Gly Lys Ser Leu Leu Asn Gly Leu Glu Asn Leu Leu Arg Asp
225             230             235             240
Leu Glu Arg Gly Gly Gly Arg Leu Arg Pro Thr Met Ser Asp Glu Thr
                245             250             255
Ala Phe Glu Val Gly Arg Thr Leu Ala Met Thr Pro Gly Lys Val Val
            260             265             270
Phe Gln Asn Ala Leu Met Gln Leu Ile Leu Tyr Ala Pro Thr Thr Pro
        275             280             285
Lys Val His Lys Arg Pro Leu Leu Val Val Pro Pro Trp Ile Asn Lys
    290             295             300
Phe Tyr Ile Leu Asp Leu Thr Glu Lys Asn Ser Leu Ile Lys Tyr Met
305             310             315             320
Val Asp Gln Gly Phe Ser Val Phe Val Ile Ser Trp Val Asn Pro Asp
                325             330             335
Ala Gly Leu Ala Glu Thr Arg Phe Glu Asp Tyr Leu Ser Gln Gly Pro
            340             345             350
Leu Ala Ala Met Glu Val Met Thr Glu Ile Thr Gly Gln Arg Ala Leu
        355             360             365
Gly Leu Val Gly Tyr Cys Ile Gly Gly Thr Leu Thr Ala Cys Thr Leu
    370             375             380
Ala Val Leu Ala Ala Arg Arg Asp His Arg Val Lys Ser Ala Thr Leu
385             390             395             400
Leu Thr Thr Leu Val Asp Phe Ser Glu Pro Gly Glu Leu Gly Val Phe
                405             410             415
Ile Asp Pro Pro Leu Leu Asp Ala Leu Asp Asp Gln Met Ala Arg Asp
            420             425             430
Gly Gly Leu Asp Gly Asp Leu Leu Ser Met Ala Phe Asn Met Leu Arg
        435             440             445
Asp Asn Asp Leu Ile Trp Ser Val Phe Ile Asn Asn Tyr Leu Leu Gly
    450             455             460
Lys Thr Pro Ala Ala Phe Asp Leu Leu Tyr Trp Asn Gly Asp Ser Thr
465             470             475             480
Arg Met Pro Ala Ala Met Gln Arg Tyr Tyr Leu Arg Glu Met Tyr Gln
                485             490             495
Lys Asn Lys Leu Val Gln Pro Gly Gly Leu Thr Val Leu Gly His Ala
            500             505             510
Leu Asp Leu Arg Arg Ile Arg Thr Pro Val Tyr Leu Leu Ser Ala Arg
        515             520             525
Asp Asp His Ile Ala Pro Trp Thr Ser Thr Phe Lys Ala Thr Gly Leu
    530             535             540
Tyr Gly Gly Pro Leu Arg Phe Val Leu Ala Gly Ser Gly His Ile Ala
545             550             555             560
Gly Val Ile Asn Pro Pro Ala Lys Ala Arg Tyr Gly Tyr Trp Thr Asn
                565             570             575
Ala Asp Thr Ser Leu Glu Ala Glu Ser Trp Leu Glu Gly Ala Thr Pro
            580             585             590
```

His Gly Gly Ser Trp Trp Pro Asp Trp Ala Ala Trp Ala Ala Gly Tyr
              595                 600                 605

Ala Gly Pro Lys Val Pro Ala Arg Asp Pro Thr Lys Ala Pro Arg Pro
            610                 615                 620

Pro Leu Glu Asp Ala Pro Gly Ser Tyr Phe Lys Val Arg Ile
625                 630                 635

(2) INFORMATION FOR SEQ ID NO:3:

(i) SEQUENCE CHARACTERISTICS:
      (A) LENGTH: 600 amino acids
      (B) TYPE: amino acid
      (C) STRANDEDNESS:
      (D) TOPOLOGY: linear (xi) SEQUENCE DESCRIPTION: SEQ ID NO:3:

Met Thr Asp Thr Arg Ala Glu Ala Asp Leu Thr Glu Val Trp Arg Ala
1               5                   10                  15

Trp Ala Ala Trp Gly Glu Lys Ser Arg Thr Met Trp Ala Thr Ala Leu
            20                  25                  30

Gly Gly Ala Ala Pro Pro Ser Ser Pro Ser Pro Ser Gly Pro Asp Pro
            35                  40                  45

Ala Val Gly Gly Gly Pro Ala Val Gly Gly Asp Ala Ala Arg Ala Phe
    50                  55                  60

Leu Glu Gly Val Leu Arg Pro Ser Gln Pro Val Leu Asp Ala Gln Ala
65                  70                  75                  80

Ala Trp Ala Arg Asp Ile Ala Ala Leu Cys Gln Ala Ala Ala Lys Arg
                85                  90                  95

Leu Arg Gly Glu Glu Ala Ala Pro Val Ile Glu Pro Ala Gly Asp Asp
                100                 105                 110

Asn Arg Phe Lys Asp Asp Ala Trp Thr Lys Asp Pro Leu Phe Asp Thr
            115                 120                 125

Leu Lys Gln Gly Tyr Leu Leu Thr Ala Arg Leu Val Ala Thr Thr Leu
    130                 135                 140

Glu Asn Ser Gly Gly Asp Pro Ala Cys Arg Gln Arg Leu Ala Phe Tyr
145                 150                 155                 160

Gly Arg Gln Val Val Asp Ala Leu Ala Pro Thr Asn Phe Ala Ala Thr
                165                 170                 175

Asn Pro Leu Val Arg Arg Thr Ala Leu Glu Ser Gly Gly Lys Ser Leu
            180                 185                 190

Leu Asn Gly Leu Glu Asn Leu Leu Arg Asp Leu Glu Arg Gly Gly Gly
    195                 200                 205

Arg Leu Arg Pro Thr Met Ser Asp Glu Thr Ala Phe Glu Val Gly Arg
        210                 215                 220

Thr Leu Ala Met Thr Pro Gly Lys Val Val Phe Gln Asn Ala Leu Met
225                 230                 235                 240

Gln Leu Ile Leu Tyr Ala Pro Thr Thr Pro Lys Val His Lys Arg Pro
                245                 250                 255

Leu Leu Val Val Pro Pro Trp Ile Asn Lys Phe Tyr Ile Leu Asp Leu
            260                 265                 270

Thr Glu Lys Asn Ser Leu Ile Lys Tyr Met Val Asp Gln Gly Phe Ser
    275                 280                 285

Val Phe Val Ile Ser Trp Val Asn Pro Asp Ala Gly Leu Ala Glu Thr
    290                 295                 300

Arg Phe Glu Asp Tyr Leu Ser Gln Gly Pro Leu Ala Ala Met Glu Val
305                 310                 315                 320

```
Met  Thr  Glu  Ile  Thr  Gly  Gln  Arg  Ala  Leu  Gly  Leu  Val  Gly  Tyr  Cys
               325                      330                     335

Ile  Gly  Gly  Thr  Leu  Thr  Ala  Cys  Thr  Leu  Ala  Val  Leu  Ala  Ala  Arg
               340                      345                     350

Arg  Asp  His  Arg  Val  Lys  Ser  Ala  Thr  Leu  Leu  Thr  Thr  Leu  Val  Asp
          355                      360                     365

Phe  Ser  Glu  Pro  Gly  Glu  Leu  Gly  Val  Phe  Ile  Asp  Pro  Pro  Leu  Leu
     370                     375                     380

Asp  Ala  Leu  Asp  Asp  Gln  Met  Ala  Arg  Asp  Gly  Gly  Leu  Asp  Gly  Asp
385                      390                     395                          400

Leu  Leu  Ser  Met  Ala  Phe  Asn  Met  Leu  Arg  Asp  Asn  Asp  Leu  Ile  Trp
               405                      410                     415

Ser  Val  Phe  Ile  Asn  Asn  Tyr  Leu  Leu  Gly  Lys  Thr  Pro  Ala  Ala  Phe
               420                      425                     430

Asp  Leu  Leu  Tyr  Trp  Asn  Gly  Asp  Ser  Thr  Arg  Met  Pro  Ala  Ala  Met
          435                      440                     445

Gln  Arg  Tyr  Tyr  Leu  Arg  Glu  Met  Tyr  Gln  Lys  Asn  Lys  Leu  Val  Gln
     450                     455                     460

Pro  Gly  Gly  Leu  Thr  Val  Leu  Gly  His  Ala  Leu  Asp  Leu  Arg  Arg  Ile
465                      470                     475                          480

Arg  Thr  Pro  Val  Tyr  Leu  Leu  Ser  Ala  Arg  Asp  Asp  His  Ile  Ala  Pro
               485                      490                     495

Trp  Thr  Ser  Thr  Phe  Lys  Ala  Thr  Gly  Leu  Tyr  Gly  Gly  Pro  Leu  Arg
               500                      505                     510

Phe  Val  Leu  Ala  Gly  Ser  Gly  His  Ile  Ala  Gly  Val  Ile  Asn  Pro  Pro
          515                      520                     525

Ala  Lys  Ala  Arg  Tyr  Gly  Tyr  Trp  Thr  Asn  Ala  Asp  Thr  Ser  Leu  Glu
     530                     535                     540

Ala  Glu  Ser  Trp  Leu  Glu  Gly  Ala  Thr  Pro  His  Gly  Gly  Ser  Trp  Trp
545                      550                     555                          560

Pro  Asp  Trp  Ala  Ala  Trp  Ala  Ala  Gly  Tyr  Ala  Gly  Pro  Lys  Val  Pro
               565                      570                     575

Ala  Arg  Asp  Pro  Thr  Lys  Ala  Pro  Arg  Pro  Pro  Leu  Glu  Asp  Ala  Pro
               580                      585                     590

Gly  Ser  Tyr  Phe  Lys  Val  Arg  Ile
          595                      600
```

( 2 ) INFORMATION FOR SEQ ID NO:4:

( i ) SEQUENCE CHARACTERISTICS:
        ( A ) LENGTH: 574 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

```
Met  Trp  Ala  Thr  Ala  Leu  Gly  Gly  Ala  Ala  Pro  Pro  Ser  Ser  Pro  Ser
1                   5                        10                      15

Pro  Ser  Gly  Pro  Asp  Pro  Ala  Val  Gly  Gly  Pro  Ala  Val  Gly  Gly
               20                      25                      30

Asp  Ala  Ala  Arg  Ala  Phe  Leu  Glu  Gly  Val  Leu  Arg  Pro  Ser  Gln  Pro
          35                      40                      45

Val  Leu  Asp  Ala  Gln  Ala  Ala  Trp  Ala  Arg  Asp  Ile  Ala  Ala  Leu  Cys
     50                      55                      60

Gln  Ala  Ala  Ala  Lys  Arg  Leu  Arg  Gly  Glu  Glu  Ala  Ala  Pro  Val  Ile
65                       70                      75                           80
```

```
Glu  Pro  Ala  Gly  Asp  Asp  Asn  Arg  Phe  Lys  Asp  Asp  Ala  Trp  Thr  Lys
               85                      90                      95

Asp  Pro  Leu  Phe  Asp  Thr  Leu  Lys  Gln  Gly  Tyr  Leu  Leu  Thr  Ala  Arg
                    100                      105                     110

Leu  Val  Ala  Thr  Thr  Leu  Glu  Asn  Ser  Gly  Gly  Asp  Pro  Ala  Cys  Arg
               115                      120                     125

Gln  Arg  Leu  Ala  Phe  Tyr  Gly  Arg  Gln  Val  Val  Asp  Ala  Leu  Ala  Pro
     130                     135                          140

Thr  Asn  Phe  Ala  Ala  Thr  Asn  Pro  Leu  Val  Arg  Arg  Thr  Ala  Leu  Glu
145                      150                     155                     160

Ser  Gly  Gly  Lys  Ser  Leu  Leu  Asn  Gly  Leu  Glu  Asn  Leu  Leu  Arg  Asp
                    165                      170                     175

Leu  Glu  Arg  Gly  Gly  Gly  Arg  Leu  Arg  Pro  Thr  Met  Ser  Asp  Glu  Thr
                    180                      185                     190

Ala  Phe  Glu  Val  Gly  Arg  Thr  Leu  Ala  Met  Thr  Pro  Gly  Lys  Val  Val
               195                      200                     205

Phe  Gln  Asn  Ala  Leu  Met  Gln  Leu  Ile  Leu  Tyr  Ala  Pro  Thr  Thr  Pro
     210                     215                          220

Lys  Val  His  Lys  Arg  Pro  Leu  Leu  Val  Val  Pro  Pro  Trp  Ile  Asn  Lys
225                      230                     235                     240

Phe  Tyr  Ile  Leu  Asp  Leu  Thr  Glu  Lys  Asn  Ser  Leu  Ile  Lys  Tyr  Met
                    245                      250                     255

Val  Asp  Gln  Gly  Phe  Ser  Val  Phe  Val  Ile  Ser  Trp  Val  Asn  Pro  Asp
                    260                      265                     270

Ala  Gly  Leu  Ala  Glu  Thr  Arg  Phe  Glu  Asp  Tyr  Leu  Ser  Gln  Gly  Pro
          275                      280                     285

Leu  Ala  Ala  Met  Glu  Val  Met  Thr  Glu  Ile  Thr  Gly  Gln  Arg  Ala  Leu
     290                     295                          300

Gly  Leu  Val  Gly  Tyr  Cys  Ile  Gly  Gly  Thr  Leu  Thr  Ala  Cys  Thr  Leu
305                           310                     315                     320

Ala  Val  Leu  Ala  Ala  Arg  Arg  Asp  His  Arg  Val  Lys  Ser  Ala  Thr  Leu
                    325                      330                     335

Leu  Thr  Thr  Leu  Val  Asp  Phe  Ser  Glu  Pro  Gly  Glu  Leu  Gly  Val  Phe
               340                      345                     350

Ile  Asp  Pro  Pro  Leu  Leu  Asp  Ala  Leu  Asp  Asp  Gln  Met  Ala  Arg  Asp
          355                      360                     365

Gly  Gly  Leu  Asp  Gly  Asp  Leu  Leu  Ser  Met  Ala  Phe  Asn  Met  Leu  Arg
          370                     375                     380

Asp  Asn  Asp  Leu  Ile  Trp  Ser  Val  Phe  Ile  Asn  Asn  Tyr  Leu  Leu  Gly
385                           390                     395                     400

Lys  Thr  Pro  Ala  Ala  Phe  Asp  Leu  Leu  Tyr  Trp  Asn  Gly  Asp  Ser  Thr
                    405                     410                     415

Arg  Met  Pro  Ala  Ala  Met  Gln  Arg  Tyr  Tyr  Leu  Arg  Glu  Met  Tyr  Gln
                    420                     425                     430

Lys  Asn  Lys  Leu  Val  Gln  Pro  Gly  Gly  Leu  Thr  Val  Leu  Gly  His  Ala
          435                     440                     445

Leu  Asp  Leu  Arg  Arg  Ile  Arg  Thr  Pro  Val  Tyr  Leu  Leu  Ser  Ala  Arg
     450                     455                     460

Asp  Asp  His  Ile  Ala  Pro  Trp  Thr  Ser  Thr  Phe  Lys  Ala  Thr  Gly  Leu
465                           470                     475                     480

Tyr  Gly  Gly  Pro  Leu  Arg  Phe  Val  Leu  Ala  Gly  Ser  Gly  His  Ile  Ala
                    485                     490                     495

Gly  Val  Ile  Asn  Pro  Pro  Ala  Lys  Ala  Arg  Tyr  Gly  Tyr  Trp  Thr  Asn
```

|     |     |     |     | 500 |     |     |     |     | 505 |     |     |     |     | 510 |
| --- | --- | --- | --- | --- | --- | --- | --- | --- | --- | --- | --- | --- | --- | --- |
| Ala | Asp | Thr | Ser | Leu | Glu | Ala | Glu | Ser | Trp | Leu | Glu | Gly | Ala | Thr | Pro |
|     |     |     | 515 |     |     |     | 520 |     |     |     | 525 |     |     |     |
| His | Gly | Gly | Ser | Trp | Trp | Pro | Asp | Trp | Ala | Ala | Trp | Ala | Ala | Gly | Tyr |
|     |     | 530 |     |     |     | 535 |     |     |     | 540 |     |     |     |     |
| Ala | Gly | Pro | Lys | Val | Pro | Ala | Arg | Asp | Pro | Thr | Lys | Ala | Pro | Arg | Pro |
| 545 |     |     |     |     | 550 |     |     |     | 555 |     |     |     |     |     | 560 |
| Pro | Leu | Glu | Asp | Ala | Pro | Gly | Ser | Tyr | Phe | Lys | Val | Arg | Ile |     |     |
|     |     |     |     | 565 |     |     |     |     | 570 |     |     |     |     |     |     |

( 2 ) INFORMATION FOR SEQ ID NO:5:

( i ) SEQUENCE CHARACTERISTICS:
        ( A ) LENGTH: 589 amino acids
        ( B ) TYPE: amino acid
        ( C ) STRANDEDNESS:
        ( D ) TOPOLOGY: linear ( x i ) SEQUENCE DESCRIPTION: SEQ ID NO:5:

| Met | Ala | Thr | Gly | Lys | Gly | Ala | Ala | Ala | Ser | Thr | Gln | Glu | Gly | Lys | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Pro | Phe | Lys | Val | Thr | Pro | Gly | Pro | Phe | Asp | Pro | Ala | Thr | Trp | Leu |
|     |     |     | 20  |     |     |     | 25  |     |     |     |     |     | 30  |     |     |
| Glu | Trp | Ser | Arg | Gln | Trp | Gln | Gly | Thr | Glu | Gly | Asn | Gly | His | Ala | Ala |
|     |     | 35  |     |     |     |     | 40  |     |     |     |     | 45  |     |     |     |
| Ala | Ser | Gly | Ile | Pro | Gly | Leu | Asp | Ala | Leu | Ala | Gly | Val | Lys | Ile | Ala |
|     | 50  |     |     |     |     | 55  |     |     |     |     | 60  |     |     |     |     |
| Pro | Ala | Gln | Leu | Gly | Asp | Ile | Gln | Gln | Arg | Tyr | Met | Lys | Asp | Phe | Ser |
| 65  |     |     |     |     | 70  |     |     |     |     | 75  |     |     |     |     | 80  |
| Ala | Leu | Trp | Gln | Ala | Met | Ala | Glu | Gly | Lys | Ala | Glu | Ala | Thr | Gly | Pro |
|     |     |     |     | 85  |     |     |     |     | 90  |     |     |     |     | 95  |     |
| Leu | His | Asp | Arg | Arg | Phe | Ala | Gly | Asp | Ala | Trp | Arg | Thr | Asn | Leu | Pro |
|     |     |     | 100 |     |     |     |     | 105 |     |     |     |     | 110 |     |     |
| Tyr | Arg | Phe | Ala | Ala | Ala | Phe | Tyr | Leu | Leu | Asn | Ala | Arg | Ala | Leu | Thr |
|     |     | 115 |     |     |     |     | 120 |     |     |     |     | 125 |     |     |     |
| Glu | Leu | Ala | Asp | Ala | Val | Glu | Ala | Asp | Ala | Lys | Thr | Arg | Gln | Arg | Ile |
|     | 130 |     |     |     |     | 135 |     |     |     |     | 140 |     |     |     |     |
| Arg | Phe | Ala | Ile | Ser | Gln | Trp | Val | Asp | Ala | Met | Ser | Pro | Ala | Asn | Phe |
| 145 |     |     |     |     | 150 |     |     |     |     | 155 |     |     |     |     | 160 |
| Leu | Ala | Thr | Asn | Pro | Glu | Ala | Gln | Arg | Leu | Leu | Ile | Glu | Ser | Gly | Gly |
|     |     |     |     | 165 |     |     |     |     | 170 |     |     |     |     | 175 |     |
| Glu | Ser | Leu | Arg | Ala | Gly | Val | Arg | Asn | Met | Met | Glu | Asp | Leu | Thr | Arg |
|     |     |     |     | 180 |     |     |     | 185 |     |     |     |     | 190 |     |     |
| Gly | Lys | Ile | Ser | Gln | Thr | Asp | Glu | Ser | Ala | Phe | Glu | Val | Gly | Arg | Asn |
|     |     | 195 |     |     |     |     | 200 |     |     |     |     | 205 |     |     |     |
| Val | Ala | Val | Thr | Glu | Gly | Ala | Val | Val | Phe | Glu | Asn | Glu | Tyr | Phe | Gln |
|     | 210 |     |     |     |     | 215 |     |     |     |     | 220 |     |     |     |     |
| Leu | Leu | Gln | Tyr | Lys | Pro | Leu | Thr | Asp | Lys | Val | His | Ala | Arg | Pro | Leu |
| 225 |     |     |     |     | 230 |     |     |     |     | 235 |     |     |     |     | 240 |
| Leu | Met | Val | Pro | Pro | Cys | Ile | Asn | Lys | Tyr | Tyr | Ile | Leu | Asp | Leu | Gln |
|     |     |     |     | 245 |     |     |     |     | 250 |     |     |     |     | 255 |     |
| Pro | Glu | Ser | Ser | Leu | Val | Arg | His | Val | Val | Glu | Gln | Gly | His | Thr | Val |
|     |     |     | 260 |     |     |     |     | 265 |     |     |     |     | 270 |     |     |
| Phe | Leu | Val | Ser | Trp | Arg | Asn | Pro | Asp | Ala | Ser | Met | Ala | Gly | Ser | Thr |
|     |     | 275 |     |     |     |     | 280 |     |     |     |     | 285 |     |     |     |
| Trp | Asp | Asp | Tyr | Ile | Glu | His | Ala | Ala | Ile | Arg | Ala | Ile | Glu | Val | Ala |

|   |   |   |   | 290 |   |   |   |   | 295 |   |   |   |   | 300 |   |   |
|---|---|---|---|---|---|---|---|---|---|---|---|---|---|---|---|---|

Arg Asp Ile Ser Gly Gln Asp Lys Ile Asn Val Leu Gly Phe Cys Val
305                     310                     315                     320

Gly Gly Thr Ile Val Ser Thr Ala Leu Ala Val Leu Ala Ala Arg Gly
                    325                     330                     335

Glu His Pro Ala Ala Ser Val Thr Leu Leu Thr Thr Leu Leu Asp Phe
                340                     345                     350

Ala Asp Thr Gly Ile Leu Asp Val Phe Val Asp Glu Gly His Val Gln
            355                     360                     365

Leu Arg Glu Ala Thr Leu Gly Gly Gly Ala Gly Ala Pro Cys Ala Leu
        370                     375                     380

Leu Arg Gly Leu Glu Leu Ala Asn Thr Phe Ser Phe Leu Arg Pro Asn
385                     390                     395                     400

Asp Leu Val Trp Asn Tyr Val Val Asp Asn Tyr Leu Lys Gly Asn Thr
                405                     410                     415

Pro Val Pro Phe Asp Leu Leu Phe Trp Asn Gly Asp Ala Thr Asn Leu
            420                     425                     430

Pro Gly Pro Trp Tyr Cys Trp Tyr Leu Arg His Thr Tyr Leu Gln Asn
        435                     440                     445

Glu Leu Lys Val Pro Gly Lys Leu Thr Val Cys Gly Val Pro Val Asp
    450                     455                     460

Leu Ala Ser Ile Asp Val Pro Thr Tyr Ile Tyr Gly Ser Arg Glu Asp
465                     470                     475                     480

His Ile Val Pro Trp Thr Ala Ala Tyr Ala Ser Thr Ala Leu Leu Ala
                485                     490                     495

Asn Lys Leu Arg Phe Val Leu Gly Ala Ser Gly His Ile Ala Gly Val
            500                     505                     510

Ile Asn Pro Pro Ala Lys Asn Lys Arg Ser His Trp Thr Asn Asp Ala
        515                     520                     525

Leu Pro Glu Ser Pro Gln Gln Trp Leu Ala Gly Ala Ile Glu His His
    530                     535                     540

Gly Ser Trp Trp Pro Asp Trp Thr Ala Trp Leu Ala Gly Gln Ala Gly
545                     550                     555                     560

Ala Lys Arg Ala Ala Pro Ala Asn Tyr Gly Asn Ala Arg Tyr Arg Ala
                565                     570                     575

Ile Glu Pro Ala Pro Gly Arg Tyr Val Lys Ala Lys Ala
            580                     585

( 2 ) INFORMATION FOR SEQ ID NO:6:

( i ) SEQUENCE CHARACTERISTICS:
        ( A ) LENGTH: 604 amino acids
        ( B ) TYPE: amino acid
        ( C ) STRANDEDNESS:
        ( D ) TOPOLOGY: linear ( x i ) SEQUENCE DESCRIPTION: SEQ ID NO:6:

Val Gly Thr Glu Arg Thr Asn Pro Ala Ala Pro Asp Phe Glu Thr Ile
1               5                   10                  15

Ala Arg Asn Ala Asn Gln Leu Ala Glu Val Phe Arg Gln Ser Ala Ala
            20                  25                  30

Ala Ser Leu Lys Pro Phe Glu Pro Ala Gly Gln Gly Ala Leu Leu Pro
        35                  40                  45

Gly Ala Asn Leu Gln Gly Ala Ser Glu Ile Asp Glu Met Thr Arg Thr
    50                  55                  60

Leu Thr Arg Val Ala Glu Thr Trp Leu Lys Asp Pro Glu Lys Ala Leu

```
          65                      70                      75                      80
Gln  Ala  Gln  Thr  Lys  Leu  Gly  Gln  Ser  Phe  Ala  Ala  Leu  Trp  Ala  Ser
                     85                      90                      95

Thr  Leu  Thr  Arg  Met  Gln  Gly  Ala  Val  Thr  Glu  Pro  Val  Val  Gln  Pro
               100                     105                     110

Pro  Pro  Thr  Asp  Lys  Arg  Phe  Ala  His  Ala  Asp  Trp  Ser  Ala  Asn  Pro
               115                     120                     125

Val  Phe  Asp  Leu  Ile  Lys  Gln  Ser  Tyr  Leu  Leu  Gly  Arg  Trp  Ala
          130                     135                     140

Glu  Glu  Met  Val  Glu  Thr  Ala  Glu  Gly  Ile  Asp  Glu  His  Thr  Arg  His
145                     150                     155                          160

Lys  Ala  Glu  Phe  Tyr  Leu  Arg  Gln  Leu  Leu  Ser  Ala  Tyr  Ser  Pro  Ser
               165                     170                     175

Asn  Phe  Val  Met  Thr  Asn  Pro  Glu  Leu  Leu  Arg  Gln  Thr  Leu  Glu  Glu
               180                     185                     190

Gly  Gly  Ala  Asn  Leu  Met  Arg  Gly  Met  Lys  Met  Leu  Gln  Glu  Asp  Leu
          195                     200                     205

Glu  Ala  Gly  Gly  Gly  Gln  Leu  Arg  Val  Arg  Gln  Thr  Asp  Leu  Ser  Ala
     210                     215                     220

Phe  Thr  Phe  Gly  Lys  Asp  Val  Ala  Val  Thr  Pro  Gly  Glu  Val  Ile  Phe
225                     230                     235                          240

Arg  Asn  Asp  Leu  Met  Glu  Leu  Ile  Gln  Tyr  Ala  Pro  Thr  Thr  Glu  Thr
               245                     250                     255

Val  Leu  Lys  Arg  Pro  Leu  Leu  Ile  Val  Pro  Pro  Trp  Ile  Asn  Lys  Phe
               260                     265                     270

Tyr  Ile  Leu  Asp  Leu  Asn  Pro  Gln  Lys  Ser  Leu  Ile  Gly  Trp  Met  Val
          275                     280                     285

Ser  Gln  Gly  Ile  Thr  Val  Phe  Val  Ile  Ser  Trp  Val  Asn  Pro  Asp  Glu
     290                     295                     300

Arg  His  Arg  Asp  Lys  Asp  Phe  Glu  Ser  Tyr  Met  Arg  Glu  Gly  Ile  Glu
305                     310                     315                          320

Thr  Ala  Ile  Asp  Met  Ile  Gly  Val  Ala  Thr  Gly  Glu  Thr  Asp  Val  Ala
               325                     330                     335

Ala  Ala  Gly  Tyr  Cys  Val  Gly  Gly  Thr  Leu  Leu  Ala  Val  Thr  Leu  Ala
               340                     345                     350

Tyr  Gln  Ala  Ala  Thr  Gly  Asn  Arg  Arg  Ile  Lys  Ser  Ala  Thr  Phe  Leu
          355                     360                     365

Thr  Thr  Gln  Val  Asp  Phe  Thr  His  Ala  Gly  Asp  Leu  Lys  Val  Phe  Ala
     370                     375                     380

Asp  Glu  Gly  Gln  Ile  Lys  Ala  Ile  Glu  Glu  Arg  Met  Ala  Glu  His  Gly
385                     390                     395                          400

Tyr  Leu  Glu  Gly  Ala  Arg  Met  Ala  Asn  Ala  Phe  Asn  Met  Leu  Arg  Pro
               405                     410                     415

Asn  Asp  Leu  Ile  Trp  Ser  Tyr  Val  Val  Asn  Asn  Tyr  Val  Arg  Gly  Lys
               420                     425                     430

Ala  Pro  Ala  Ala  Phe  Asp  Leu  Leu  Tyr  Trp  Asn  Ala  Asp  Ala  Thr  Arg
          435                     440                     445

Met  Pro  Ala  Ala  Asn  His  Ser  Phe  Tyr  Leu  Arg  Asn  Cys  Tyr  Leu  Asn
     450                     455                     460

Asn  Thr  Leu  Ala  Lys  Gly  Gln  Met  Val  Leu  Gly  Asn  Val  Arg  Leu  Asp
465                     470                     475                          480

Leu  Lys  Lys  Val  Lys  Val  Pro  Val  Phe  Asn  Leu  Ala  Thr  Arg  Glu  Asp
               485                     490                     495
```

-continued

|     |     |     |     |     |     |     |     |     |     |     |     |     |     |     |
| --- | --- | --- | --- | --- | --- | --- | --- | --- | --- | --- | --- | --- | --- | --- |
| His | Ile | Ala | Pro | Ala | Leu | Ser | Val | Phe | Glu | Gly | Ser | Ala | Lys | Phe | Gly |
|     |     |     | 500 |     |     |     |     | 505 |     |     |     |     | 510 |     |     |
| Gly | Lys | Val | Asp | Tyr | Val | Leu | Ala | Gly | Ser | Gly | His | Ile | Ala | Gly | Val |
|     |     | 515 |     |     |     |     | 520 |     |     |     |     | 525 |     |     |     |
| Val | Ala | Pro | Pro | Gly | Pro | Lys | Ala | Lys | Tyr | Gly | Phe | Arg | Thr | Gly | Gly |
|     |     | 530 |     |     |     | 535 |     |     |     |     | 540 |     |     |     |     |
| Pro | Ala | Arg | Gly | Arg | Phe | Glu | Asp | Trp | Val | Ala | Ala | Thr | Glu | His |
| 545 |     |     |     |     | 550 |     |     |     |     | 555 |     |     |     | 560 |
| Pro | Gly | Ser | Trp | Trp | Pro | Tyr | Trp | Tyr | Lys | Trp | Leu | Glu | Glu | Gln | Ala |
|     |     |     |     | 565 |     |     |     |     | 570 |     |     |     |     | 575 |     |
| Pro | Glu | Arg | Val | Pro | Ala | Arg | Ile | Pro | Gly | Thr | Gly | Ala | Leu | Pro | Ser |
|     |     |     |     | 580 |     |     |     |     | 585 |     |     |     | 590 |     |     |
| Leu | Ala | Pro | Ala | Pro | Gly | Thr | Tyr | Val | Arg | Met | Lys |
|     |     | 595 |     |     |     |     | 600 |     |     |     |     |

( 2 ) INFORMATION FOR SEQ ID NO:7:

( i ) SEQUENCE CHARACTERISTICS:
       ( A ) LENGTH: 559 amino acids
       ( B ) TYPE: amino acid
       ( C ) STRANDEDNESS:
       ( D ) TOPOLOGY: linear ( x i ) SEQUENCE DESCRIPTION: SEQ ID NO:7:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ser | Gln | Lys | Asn | Asn | Asn | Glu | Leu | Pro | Lys | Gln | Ala | Ala | Glu | Asn |
| 1   |     |     |     | 5   |     |     |     |     | 10  |     |     |     |     | 15  |     |
| Thr | Leu | Asn | Leu | Asn | Pro | Val | Ile | Gly | Ile | Arg | Gly | Lys | Asp | Leu | Leu |
|     |     |     | 20  |     |     |     |     | 25  |     |     |     |     | 30  |     |     |
| Thr | Ser | Ala | Arg | Met | Val | Leu | Leu | Gln | Ala | Val | Arg | Gln | Pro | Leu | His |
|     |     | 35  |     |     |     |     | 40  |     |     |     |     | 45  |     |     |     |
| Ser | Ala | Arg | His | Val | Ala | His | Phe | Ser | Leu | Glu | Leu | Lys | Asn | Val | Leu |
|     | 50  |     |     |     |     | 55  |     |     |     |     | 60  |     |     |     |     |
| Leu | Gly | Gln | Ser | Glu | Leu | Arg | Pro | Gly | Asp | Asp | Arg | Arg | Phe | Ser |
| 65  |     |     |     |     | 70  |     |     |     |     | 75  |     |     |     | 80  |
| Asp | Pro | Ala | Trp | Ser | Gln | Asn | Pro | Leu | Tyr | Lys | Arg | Tyr | Met | Gln | Thr |
|     |     |     |     | 85  |     |     |     |     | 90  |     |     |     |     | 95  |     |
| Tyr | Leu | Ala | Trp | Arg | Lys | Glu | Leu | His | Ser | Trp | Ile | Ser | His | Ser | Asp |
|     |     |     | 100 |     |     |     |     | 105 |     |     |     |     | 110 |     |     |
| Leu | Ser | Pro | Gln | Asp | Ile | Ser | Arg | Gly | Gln | Phe | Val | Ile | Asn | Leu | Leu |
|     |     | 115 |     |     |     |     | 120 |     |     |     |     | 125 |     |     |     |
| Thr | Glu | Ala | Met | Ser | Pro | Thr | Asn | Ser | Leu | Ser | Asn | Pro | Ala | Ala | Val |
|     | 130 |     |     |     |     | 135 |     |     |     |     | 140 |     |     |     |     |
| Lys | Arg | Phe | Phe | Glu | Thr | Gly | Gly | Lys | Ser | Leu | Leu | Asp | Gly | Leu | Gly |
| 145 |     |     |     |     | 150 |     |     |     |     | 155 |     |     |     |     | 160 |
| His | Leu | Ala | Lys | Asp | Leu | Val | Asn | Asn | Gly | Gly | Met | Pro | Ser | Gln | Val |
|     |     |     |     | 165 |     |     |     |     | 170 |     |     |     |     | 175 |     |
| Asp | Met | Asp | Ala | Phe | Glu | Val | Gly | Lys | Asn | Leu | Ala | Thr | Thr | Glu | Gly |
|     |     |     | 180 |     |     |     |     | 185 |     |     |     |     | 190 |     |     |
| Ala | Val | Val | Phe | Arg | Asn | Asp | Val | Leu | Glu | Leu | Ile | Gln | Tyr | Arg | Pro |
|     |     | 195 |     |     |     |     | 200 |     |     |     |     | 205 |     |     |     |
| Ile | Thr | Glu | Ser | Val | His | Glu | Arg | Pro | Leu | Leu | Val | Val | Pro | Pro | Gln |
|     | 210 |     |     |     |     | 215 |     |     |     |     | 220 |     |     |     |     |
| Ile | Asn | Lys | Phe | Tyr | Val | Phe | Asp | Leu | Ser | Pro | Asp | Lys | Ser | Leu | Ala |
| 225 |     |     |     |     | 230 |     |     |     |     | 235 |     |     |     |     | 240 |
| Arg | Phe | Cys | Leu | Arg | Asn | Gly | Val | Gln | Thr | Phe | Ile | Val | Ser | Trp | Arg |
|     |     |     |     | 245 |     |     |     |     | 250 |     |     |     |     | 255 |     |

```
Asn Pro Thr Lys Ser Gln Arg Glu Trp Gly Leu Thr Thr Tyr Ile Glu
            260             265                 270

Ala Leu Lys Glu Ala Ile Glu Val Val Leu Ser Ile Thr Gly Ser Lys
            275             280                 285

Asp Leu Asn Leu Leu Gly Ala Cys Ser Gly Gly Ile Thr Thr Ala Thr
            290             295                 300

Leu Val Gly His Tyr Val Ala Ser Gly Glu Lys Lys Val Asn Ala Phe
305             310             315                 320

Thr Gln Leu Val Ser Val Leu Asp Phe Glu Leu Asn Thr Gln Val Ala
            325             330                 335

Leu Phe Ala Asp Glu Lys Thr Leu Glu Ala Ala Lys Arg Arg Ser Tyr
            340             345                 350

Gln Ser Gly Val Leu Glu Gly Lys Asp Met Ala Lys Val Phe Ala Trp
            355             360                 365

Met Arg Pro Asn Asp Leu Ile Trp Asn Tyr Trp Val Asn Asn Tyr Leu
    370             375                 380

Leu Gly Asn Gln Pro Pro Ala Phe Asp Ile Leu Tyr Trp Asn Asn Asp
385             390             395                 400

Thr Thr Arg Leu Pro Ala Ala Leu His Gly Glu Phe Val Glu Leu Phe
            405             410                 415

Lys Ser Asn Pro Leu Asn Arg Pro Gly Ala Leu Glu Val Ser Gly Thr
            420             425                 430

Pro Ile Asp Leu Lys Gln Val Thr Cys Asp Phe Tyr Cys Val Ala Gly
            435             440                 445

Leu Asn Asp His Ile Thr Pro Trp Glu Ser Cys Tyr Lys Ser Ala Arg
            450             455                 460

Leu Leu Gly Gly Lys Cys Glu Phe Ile Leu Ser Asn Ser Gly His Ile
465             470             475                 480

Gln Ser Ile Leu Asn Pro Pro Gly Asn Pro Lys Ala Arg Phe Met Thr
            485             490                 495

Asn Pro Glu Leu Pro Ala Glu Pro Lys Ala Trp Leu Glu Gln Ala Gly
            500             505                 510

Lys His Ala Asp Ser Trp Trp Leu His Trp Gln Gln Trp Leu Ala Glu
            515             520                 525

Arg Ser Gly Lys Thr Arg Lys Ala Pro Ala Ser Leu Gly Asn Lys Thr
            530             535                 540

Tyr Pro Ala Gly Glu Ala Ala Pro Gly Thr Tyr Val His Glu Arg
545             550                 555
```

( 2 ) INFORMATION FOR SEQ ID NO:8:

( i ) SEQUENCE CHARACTERISTICS:
    ( A ) LENGTH: 560 amino acids
    ( B ) TYPE: amino acid
    ( C ) STRANDEDNESS:
    ( D ) TOPOLOGY: linear ( x i ) SEQUENCE DESCRIPTION: SEQ ID NO:8:

```
Met Arg Glu Lys Gln Glu Ser Gly Ser Val Pro Val Pro Ala Glu Phe
1               5               10                  15

Met Ser Ala Gln Ser Ala Ile Val Gly Leu Arg Gly Lys Asp Leu Leu
            20              25                  30

Thr Thr Val Arg Ser Leu Ala Val His Gly Leu Arg Gln Pro Leu His
            35              40                  45

Ser Ala Arg His Leu Val Ala Phe Gly Gly Gln Leu Gly Lys Val Leu
            50              55                  60
```

```
Leu  Gly  Asp  Thr  Leu  His  Gln  Pro  Asn  Pro  Gln  Asp  Ala  Arg  Phe  Gln
 65                  70                   75                   80

Asp  Pro  Ser  Trp  Arg  Leu  Asn  Pro  Phe  Tyr  Arg  Arg  Thr  Leu  Gln  Ala
                85                   90                   95

Tyr  Leu  Ala  Trp  Gln  Lys  Gln  Leu  Leu  Trp  Ile  Asp  Glu  Ser  Asn
               100                 105                 110

Leu  Asp  Cys  Asp  Asp  Arg  Ala  Arg  Ala  Arg  Phe  Leu  Val  Ala  Leu  Leu
               115                 120                 125

Ser  Asp  Ala  Val  Ala  Pro  Ser  Asn  Ser  Leu  Ile  Asn  Pro  Leu  Ala  Leu
     130                 135                 140

Lys  Glu  Leu  Phe  Asn  Thr  Gly  Gly  Ile  Ser  Leu  Leu  Asn  Gly  Val  Arg
145                      150                 155                          160

His  Leu  Leu  Glu  Asp  Leu  Val  His  Asn  Gly  Gly  Met  Pro  Ser  Gln  Val
                    165                 170                 175

Asn  Lys  Thr  Ala  Phe  Glu  Ile  Gly  Arg  Asn  Leu  Ala  Thr  Thr  Gln  Gly
               180                 185                 190

Ala  Val  Val  Phe  Arg  Asn  Glu  Val  Leu  Glu  Leu  Ile  Gln  Tyr  Lys  Pro
               195                 200                 205

Leu  Gly  Glu  Arg  Gln  Tyr  Ala  Lys  Pro  Leu  Leu  Ile  Val  Pro  Pro  Gln
     210                 215                 220

Ile  Asn  Lys  Tyr  Tyr  Ile  Phe  Asp  Leu  Ser  Pro  Glu  Lys  Ser  Phe  Val
225                      230                 235                          240

Gln  Tyr  Ala  Leu  Lys  Asn  Asn  Leu  Gln  Val  Phe  Val  Ile  Ser  Trp  Arg
               245                 250                 255

Asn  Pro  Asp  Ala  Gln  His  Arg  Glu  Trp  Gly  Leu  Ser  Thr  Tyr  Val  Glu
               260                 265                 270

Ala  Leu  Asp  Gln  Ala  Ile  Glu  Val  Ser  Arg  Glu  Ile  Thr  Gly  Ser  Arg
          275                 280                 285

Ser  Val  Asn  Leu  Ala  Gly  Ala  Cys  Ala  Gly  Gly  Leu  Thr  Val  Ala  Ala
     290                 295                 300

Leu  Leu  Gly  His  Leu  Gln  Val  Arg  Arg  Gln  Leu  Arg  Lys  Val  Ser  Ser
305                      310                 315                          320

Val  Thr  Tyr  Leu  Val  Ser  Leu  Leu  Asp  Ser  Gln  Met  Glu  Ser  Pro  Ala
                    325                 330                 335

Met  Leu  Phe  Ala  Asp  Glu  Gln  Thr  Leu  Glu  Ser  Ser  Lys  Arg  Arg  Ser
               340                 345                 350

Tyr  Gln  His  Gly  Val  Leu  Asp  Gly  Arg  Asp  Met  Ala  Lys  Val  Phe  Ala
          355                 360                 365

Trp  Met  Arg  Pro  Asn  Asp  Leu  Ile  Trp  Asn  Tyr  Trp  Val  Asn  Asn  Tyr
     370                 375                 380

Leu  Leu  Gly  Arg  Gln  Pro  Pro  Ala  Phe  Asp  Ile  Leu  Tyr  Trp  Asn  Asn
385                      390                 395                          400

Asp  Asn  Thr  Arg  Leu  Pro  Ala  Ala  Phe  His  Gly  Glu  Leu  Leu  Asp  Leu
                    405                 410                 415

Phe  Lys  His  Asn  Pro  Leu  Thr  Arg  Pro  Gly  Ala  Leu  Glu  Val  Ser  Gly
               420                 425                 430

Thr  Ala  Val  Asp  Leu  Gly  Lys  Val  Ala  Ile  Asp  Ser  Phe  His  Val  Ala
               435                 440                 445

Gly  Ile  Thr  Asp  His  Ile  Thr  Pro  Trp  Asp  Ala  Val  Tyr  Arg  Ser  Ala
          450                 455                 460

Leu  Leu  Leu  Gly  Gly  Gln  Arg  Arg  Phe  Ile  Leu  Ser  Asn  Ser  Gly  His
465                      470                 475                          480

Ile  Gln  Ser  Ile  Leu  Asn  Pro  Pro  Gly  Asn  Pro  Lys  Ala  Cys  Tyr  Phe
               485                 490                 495
```

| | | | | | | | | | | | | | | |
|---|---|---|---|---|---|---|---|---|---|---|---|---|---|---|
| Glu | Asn | Asp | Lys<br>500 | Leu | Ser | Ser | Asp | Pro<br>505 | Arg | Ala | Trp | Tyr | Tyr<br>510 | Asp | Ala |
| Lys | Arg | Glu<br>515 | Glu | Gly | Ser | Trp | Trp<br>520 | Pro | Val | Trp | Leu | Gly<br>525 | Trp | Leu | Gln |
| Glu | Arg<br>530 | Ser | Gly | Glu | Leu | Gly<br>535 | Asn | Pro | Asp | Phe | Asn<br>540 | Leu | Gly | Ser | Ala |
| Ala<br>545 | His | Pro | Pro | Leu | Glu<br>550 | Ala | Ala | Pro | Gly | Thr<br>555 | Tyr | Val | His | Ile | Arg<br>560 |

( 2 ) INFORMATION FOR SEQ ID NO:9:

( i ) SEQUENCE CHARACTERISTICS:
        ( A ) LENGTH: 624 amino acids
        ( B ) TYPE: amino acid
        ( C ) STRANDEDNESS:
        ( D ) TOPOLOGY: linear ( x i ) SEQUENCE DESCRIPTION: SEQ ID NO:9:

| | | | | | | | | | | | | | | |
|---|---|---|---|---|---|---|---|---|---|---|---|---|---|---|
| Met<br>1 | Ala | Ala | Pro | Arg<br>5 | Ala | Gln | Ala | Ala | Ala<br>10 | Pro | Ala | Gly | Thr | Gly<br>15 | Gln |
| Ser | Ala | Gly | Leu<br>20 | Ala | Ala | Glu | Pro | His<br>25 | Pro | Ala | Arg | Thr | Pro<br>30 | Pro | Pro |
| Ser | Ser | Arg<br>35 | Arg | Pro | Ser | Val | Pro<br>40 | Ala | Ala | Ala | Ser | Gln<br>45 | Gln | Leu | Ala |
| Gln | Asn<br>50 | Ile | Glu | Arg | Ile | Glu<br>55 | Ser | Leu | Thr | Gln | Arg<br>60 | Leu | Ile | Ser | Ala |
| Leu<br>65 | Ala | Gln | Arg | Arg | Pro<br>70 | Ser | Asn | Pro | Gly | Val<br>75 | Glu | Met | Pro | Gly | Pro<br>80 |
| Asp | Leu | Phe | Ala | Thr<br>85 | Ala | Thr | Ser | Ala | Trp<br>90 | Ile | Lys | Leu | Leu | Ala<br>95 | Glu |
| Gln | Pro | Glu | Arg<br>100 | Val | Ile | Gly | Gln | Gln<br>105 | Val | Ser | Tyr | Trp | Gly<br>110 | Glu | Thr |
| Leu | Arg | His<br>115 | Phe | Ala | Glu | Ala | Gln<br>120 | Ala | Ala | Phe | Ala | Arg<br>125 | Gly | Thr | Val |
| Thr | Pro<br>130 | Pro | Pro | Ser | Glu | Gly<br>135 | Pro | Arg | Asp | Arg | Arg<br>140 | Phe | Ala | Asn | Pro |
| Leu<br>145 | Trp | Glu | Ala | His | Pro<br>150 | Phe | Phe | Asn | Phe | Ile<br>155 | Lys | Arg | Gln | Tyr | Gln<br>160 |
| Ile | Asn | Ala | Gln | Ala<br>165 | Leu | Gln | Glu | Ala | Ala<br>170 | Ser | Thr | Leu | Asp | Leu<br>175 | Pro |
| Glu | Met | Thr | Asp<br>180 | Arg | Arg | Arg | Ile | Glu<br>185 | Trp | Phe | Thr | Arg | Gln<br>190 | Met | Ile |
| Asp | Met | Met<br>195 | Ala | Pro | Thr | Asn | Phe<br>200 | Leu | Ala | Thr | Asn | Pro<br>205 | Asp | Asp | Ser |
| Trp | Lys<br>210 | Arg | Arg | Trp | Arg | Pro<br>215 | Arg | Asp | Glu | Ser | Leu<br>220 | Val | Arg | Gly | Leu |
| Glu<br>225 | Asn | Leu | Val | Arg | Asp<br>230 | Val | Glu | Gln | Asn | Ser<br>235 | Gly | Glu | Leu | Ile | Val<br>240 |
| Ser | Leu | Ala | Asp | Arg<br>245 | Asp | Ala | Phe | Arg | Val<br>250 | Gly | Glu | Asn | Ile | Gly<br>255 | Thr |
| Thr | Glu | Gly | Thr<br>260 | Val | Val | Ala | Arg | Thr<br>265 | Lys | Leu | Tyr | Glu | Leu<br>270 | Ile | Gln |
| Tyr | Lys | Pro<br>275 | Thr | Thr | Ala | Gln | Val<br>280 | His | Glu | Ile | Pro | Leu<br>285 | Val | Ile | Phe |
| Pro | Pro<br>290 | Trp | Ile | Asn | Lys | Phe<br>295 | Tyr | Ile | Leu | Asp | Leu<br>300 | Lys | Pro | Gln | Asn |

Ser  Leu  Ile  Lys  Trp  Ile  Val  Asp  Gln  Gly  His  Thr  Leu  Phe  Val  Val
305                 310                 315                           320

Ala  Trp  Lys  Asn  Pro  Asp  Pro  Ser  Tyr  Gly  Asp  Thr  Gly  Met  Asp  Asp
                325                 330                      335

Tyr  Val  Ser  Ala  Tyr  Leu  Glu  Val  Met  Asp  Arg  Val  Leu  Asp  Leu  Thr
               340                 345                      350

Asp  Gln  Lys  Lys  Leu  Asn  Ala  Val  Gly  Tyr  Cys  Ile  Ala  Gly  Thr  Thr
               355                 360                      365

Leu  Ala  Leu  Thr  Pro  Val  Val  Leu  Lys  Gln  Arg  Gly  Asp  Asp  Arg  Val
     370                 375                      380

Asn  Ala  Ala  Thr  Phe  Phe  Thr  Ala  Leu  Thr  Asp  Phe  Ala  Asp  Gln  Gly
385                 390                      395                           400

Glu  Phe  Thr  Ala  Tyr  Leu  Gln  Asp  Phe  Val  Ser  Gly  Ile  Glu  Glu
                    405                 410                      415

Glu  Ala  Ala  Arg  Thr  Gly  Ile  Leu  Gly  Ala  Gln  Leu  Met  Thr  Arg  Thr
               420                 425                      430

Phe  Ser  Phe  Leu  Arg  Ala  Asn  Asp  Leu  Val  Trp  Gly  Pro  Ala  Ile  Arg
          435                 440                      445

Ser  Tyr  Met  Leu  Gly  Glu  Thr  Pro  Ala  Phe  Asp  Leu  Leu  Phe  Trp
     450                 455                      460

Asn  Gly  Asp  Gly  Thr  Asn  Leu  Pro  Gly  Arg  Met  Ala  Val  Glu  Tyr  Leu
465                 470                      475                           480

Arg  Gly  Leu  Cys  Gln  Gln  Asn  Arg  Phe  Val  Lys  Glu  Gly  Phe  Asp  Leu
               485                 490                      495

Met  Gly  His  Arg  Leu  His  Val  Gly  Asp  Val  Thr  Val  Pro  Leu  Cys  Ala
               500                 505                      510

Ile  Ala  Cys  Glu  Thr  Asp  His  Ile  Ala  Pro  Trp  Lys  Asp  Ser  Trp  Arg
          515                 520                      525

Gly  Ile  Ala  Gln  Met  Gly  Ser  Arg  Asp  Lys  Thr  Phe  Ile  Leu  Ser  Glu
     530                 535                      540

Ser  Gly  His  Ile  Ala  Gly  Ile  Val  Asn  Pro  Pro  Ser  Lys  Lys  Lys  Tyr
545                 550                      555                           560

Gly  His  Tyr  Thr  Ser  Asp  Ala  Gly  Phe  Gly  Gln  Gly  Glu  Gln  His  Trp
               565                 570                      575

Leu  Asp  Lys  Ala  Ser  His  His  Glu  Gly  Ser  Trp  Trp  Gly  Arg  Trp  Gly
               580                 585                      590

Glu  Trp  Leu  Ala  Arg  Arg  Ala  Gly  Gly  Met  Val  Asp  Ala  Arg  Asp  Pro
          595                 600                      605

Gly  Glu  Gly  Phe  Gly  Pro  Ala  Pro  Gly  Leu  Tyr  Val  His  Glu  Arg  Ala
     610                 615                      620

( 2 ) INFORMATION FOR SEQ ID NO:10:

( i ) SEQUENCE CHARACTERISTICS:
        ( A ) LENGTH: 559 amino acids
        ( B ) TYPE: amino acid
        ( C ) STRANDEDNESS:
        ( D ) TOPOLOGY: linear ( x i ) SEQUENCE DESCRIPTION: SEQ ID NO:10:

Met  Ser  Asn  Lys  Asn  Asn  Asp  Glu  Leu  Gln  Arg  Gln  Ala  Ser  Glu  Asn
1              5                   10                      15

Thr  Leu  Gly  Leu  Asn  Pro  Val  Ile  Gly  Ile  Arg  Arg  Lys  Asp  Leu  Leu
               20                  25                      30

Ser  Ser  Ala  Arg  Thr  Val  Leu  Arg  Gln  Ala  Val  Arg  Gln  Pro  Leu  His
               35                  40                      45

```
Ser  Ala  Lys  His  Val  Ala  His  Phe  Gly  Leu  Glu  Leu  Lys  Asn  Val  Leu
     50                  55                       60
Leu  Gly  Lys  Ser  Ser  Leu  Ala  Pro  Glu  Ser  Asp  Arg  Arg  Phe  Asn
65                       70                  75                            80
Asp  Pro  Ala  Trp  Ser  Asn  Asn  Pro  Leu  Tyr  Arg  Arg  Tyr  Leu  Gln  Thr
                    85                       90                           95
Tyr  Leu  Ala  Trp  Arg  Lys  Glu  Leu  Gln  Asp  Trp  Ile  Gly  Asn  Ser  Asp
               100                      105                      110
Leu  Ser  Pro  Gln  Asp  Ile  Ser  Arg  Gly  Gln  Phe  Val  Ile  Asn  Leu  Met
               115                 120                      125
Thr  Glu  Ala  Met  Ala  Pro  Thr  Asn  Thr  Leu  Ser  Asn  Pro  Ala  Ala  Val
     130                 135                      140
Lys  Arg  Phe  Phe  Glu  Thr  Gly  Gly  Lys  Ser  Leu  Leu  Asp  Gly  Leu  Ser
145                      150                      155                      160
Asn  Leu  Ala  Lys  Asp  Leu  Val  Asn  Asn  Gly  Gly  Met  Pro  Ser  Gln  Val
                    165                      170                      175
Asn  Met  Asp  Ala  Phe  Glu  Val  Gly  Lys  Asn  Leu  Gly  Thr  Ser  Glu  Gly
               180                      185                      190
Ala  Val  Val  Tyr  Arg  Asn  Asp  Val  Leu  Glu  Leu  Ile  Gln  Tyr  Lys  Pro
          195                      200                      205
Ile  Thr  Glu  Gln  Val  His  Ala  Arg  Pro  Leu  Leu  Val  Pro  Pro  Gln
     210                      215                      220
Ile  Asn  Lys  Phe  Tyr  Val  Phe  Asp  Leu  Ser  Pro  Glu  Lys  Ser  Leu  Ala
225                      230                      235                      240
Arg  Tyr  Cys  Leu  Arg  Ser  Gln  Gln  Gln  Thr  Phe  Ile  Ile  Ser  Trp  Arg
                    245                      250                      255
Asn  Pro  Thr  Lys  Ala  Gln  Arg  Glu  Trp  Gly  Leu  Ser  Thr  Tyr  Ile  Asp
               260                      265                      270
Ala  Leu  Lys  Glu  Ala  Val  Asp  Ala  Val  Leu  Ala  Ile  Thr  Gly  Ser  Lys
          275                      280                      285
Asp  Leu  Asn  Met  Leu  Gly  Ala  Cys  Ser  Gly  Gly  Ile  Thr  Cys  Thr  Ala
     290                      295                      300
Leu  Val  Gly  His  Tyr  Ala  Ala  Leu  Gly  Glu  Asn  Lys  Val  Asn  Ala  Leu
305                      310                      315                      320
Thr  Leu  Leu  Val  Ser  Val  Leu  Asp  Thr  Thr  Met  Asp  Asn  Gln  Val  Ala
                    325                      330                      335
Leu  Phe  Val  Asp  Glu  Gln  Thr  Leu  Glu  Ala  Ala  Lys  Arg  His  Ser  Tyr
               340                      345                      350
Gln  Ala  Gly  Val  Leu  Glu  Gly  Ser  Glu  Met  Ala  Lys  Val  Phe  Ala  Trp
          355                      360                      365
Met  Arg  Pro  Asn  Asp  Leu  Ile  Trp  Asn  Tyr  Trp  Val  Asn  Asn  Tyr  Leu
     370                      375                      380
Leu  Gly  Asn  Glu  Pro  Pro  Val  Phe  Asp  Ile  Leu  Phe  Trp  Asn  Asn  Asp
385                      390                      395                      400
Thr  Thr  Arg  Leu  Pro  Ala  Ala  Phe  His  Gly  Asp  Leu  Ile  Glu  Met  Phe
                    405                      410                      415
Lys  Ser  Asn  Pro  Leu  Thr  Arg  Pro  Asp  Ala  Leu  Glu  Val  Cys  Gly  Thr
               420                      425                      430
Pro  Ile  Asp  Leu  Lys  Gln  Val  Lys  Cys  Asp  Ile  Tyr  Ser  Leu  Ala  Gly
          435                      440                      445
Thr  Asn  Asp  His  Ile  Thr  Pro  Trp  Gln  Ser  Cys  Tyr  Arg  Ser  Ala  His
     450                      455                      460
Leu  Phe  Gly  Gly  Lys  Ile  Glu  Phe  Val  Leu  Ser  Asn  Ser  Gly  His  Ile
```

```
           465                      470                     475                      480
    Gln  Ser  Ile  Leu  Asn  Pro  Pro  Gly  Asn  Pro  Lys  Ala  Arg  Phe  Met  Thr
                        485                      490                      495

Gly  Ala  Asp  Arg  Pro  Gly  Asp  Pro  Val  Ala  Trp  Gln  Glu  Asn  Ala  Thr
                   500                      505                           510

Lys  His  Ala  Asp  Ser  Trp  Trp  Leu  His  Trp  Gln  Ser  Trp  Leu  Gly  Glu
              515                      520                      525

Arg  Ala  Gly  Glu  Leu  Glu  Lys  Ala  Pro  Thr  Arg  Leu  Gly  Asn  Arg  Ala
         530                      535                      540

Tyr  Ala  Ala  Gly  Glu  Ala  Ser  Pro  Gly  Thr  Tyr  Val  His  Glu  Arg
    545                      550                      555
```

( 2 ) INFORMATION FOR SEQ ID NO:11:

( i ) SEQUENCE CHARACTERISTICS:
        ( A ) LENGTH: 560 amino acids
        ( B ) TYPE: amino acid
        ( C ) STRANDEDNESS:
        ( D ) TOPOLOGY: linear ( x i ) SEQUENCE DESCRIPTION: SEQ ID NO:11:

```
    Met  Lys  Asp  Lys  Pro  Ala  Lys  Gly  Thr  Pro  Thr  Leu  Pro  Ala  Thr  Ser
    1                   5                        10                       15

Met  Asn  Val  Gln  Asn  Ala  Ile  Leu  Gly  Leu  Arg  Gly  Arg  Asp  Leu  Ile
                   20                       25                       30

Ser  Thr  Leu  Arg  Asn  Val  Ser  Arg  Gln  Ser  Leu  Arg  His  Pro  Leu  His
                   35                       40                       45

Thr  Ala  His  His  Leu  Leu  Ala  Leu  Gly  Gly  Gln  Leu  Gly  Arg  Val  Ile
              50                       55                       60

Leu  Gly  Asp  Thr  Pro  Leu  Gln  Pro  Asn  Pro  Arg  Asp  Pro  Arg  Phe  Ser
    65                       70                       75                       80

Asp  Pro  Thr  Trp  Ser  Gln  Asn  Pro  Phe  Tyr  Arg  Arg  Gly  Leu  Gln  Ala
                        85                       90                       95

Tyr  Leu  Ala  Trp  Gln  Lys  Gln  Thr  Arg  Leu  Trp  Ile  Glu  Glu  Ser  His
                        100                      105                      110

Leu  Asp  Asp  Asp  Asp  Arg  Ala  Arg  Ala  His  Phe  Leu  Phe  Asn  Leu  Ile
                        115                      120                      125

Asn  Asp  Ala  Leu  Ala  Pro  Ser  Asn  Ser  Leu  Leu  Asn  Pro  Leu  Ala  Val
         130                      135                      140

Lys  Glu  Leu  Phe  Asn  Ser  Gly  Gly  Gln  Ser  Leu  Val  Arg  Gly  Val  Ala
    145                      150                      155                      160

His  Leu  Leu  Asp  Asp  Leu  Arg  His  Asn  Asp  Gly  Leu  Pro  Arg  Gln  Val
                        165                      170                      175

Asp  Glu  Arg  Ala  Phe  Glu  Val  Gly  Gly  Asn  Leu  Ala  Ala  Thr  Ala  Gly
                   180                      185                      190

Ala  Val  Val  Phe  Arg  Asn  Glu  Leu  Leu  Glu  Leu  Ile  Gln  Tyr  Lys  Pro
              195                      200                      205

Met  Ser  Glu  Lys  Gln  His  Ala  Arg  Pro  Leu  Leu  Val  Val  Pro  Pro  Gln
         210                      215                      220

Ile  Asn  Lys  Phe  Tyr  Ile  Phe  Asp  Leu  Ser  Ser  Thr  Asn  Ser  Phe  Val
    225                      230                      235                      240

Gln  Tyr  Met  Leu  Lys  Asn  Gly  Leu  Gln  Val  Phe  Met  Val  Ser  Trp  Arg
                        245                      250                      255

Asn  Pro  Asp  Pro  Arg  His  Arg  Glu  Trp  Gly  Leu  Ser  Ser  Tyr  Val  Gln
                   260                      265                      270

Ala  Leu  Glu  Glu  Ala  Leu  Asn  Ala  Cys  Arg  Ser  Ile  Ser  Gly  Asn  Arg
```

-continued

|     |     |     | 275 |     |     |     | 280 |     |     |     | 285 |     |     |     |
| --- | --- | --- | --- | --- | --- | --- | --- | --- | --- | --- | --- | --- | --- | --- |
| Asp | Pro 290 | Asn | Leu | Met | Gly 295 | Ala | Cys | Ala | Gly | Gly 300 | Leu | Thr | Met | Ala | Ala |
| Leu 305 | Gln | Gly | His | Leu 310 | Gln | Ala | Lys | His 315 | Gln | Leu | Arg | Arg | Val | Arg | Ser 320 |
| Ala | Thr | Tyr | Leu | Val 325 | Ser | Leu | Leu | Asp | Ser 330 | Lys | Phe | Glu | Ser | Pro 335 | Ala |
| Ser | Leu | Phe | Ala 340 | Asp | Glu | Gln | Thr | Ile 345 | Glu | Ala | Ala | Lys | Arg 350 | Arg | Ser |
| Tyr | Gln | Arg 355 | Gly | Val | Leu | Asp | Gly 360 | Ala | Glu | Val | Ala | Arg 365 | Ile | Phe | Ala |
| Trp | Met 370 | Arg | Pro | Asn | Asp | Leu 375 | Ile | Trp | Asn | Tyr | Trp 380 | Val | Asn | Asn | Tyr |
| Leu 385 | Leu | Gly | Lys | Thr | Pro 390 | Pro | Ala | Phe | Asp | Ile 395 | Leu | Tyr | Trp | Asn | Ala 400 |
| Asp | Ser | Thr | Arg | Leu 405 | Pro | Ala | Ala | Leu | His 410 | Gly | Asp | Leu | Leu | Asp 415 | Phe |
| Phe | Lys | Leu | Asn 420 | Pro | Leu | Thr | His | Pro 425 | Ala | Gly | Leu | Glu | Val 430 | Cys | Gly |
| Thr | Pro | Ile 435 | Asp | Leu | Gln | Lys | Val 440 | Glu | Leu | Asp | Ser | Phe 445 | Thr | Val | Ala |
| Gly | Ser 450 | Asn | Asp | His | Ile | Thr 455 | Pro | Trp | Asp | Ala | Val 460 | Tyr | Arg | Ser | Ala |
| Leu 465 | Leu | Leu | Gly | Gly | Asp 470 | Arg | Arg | Phe | Val | Leu 475 | Ala | Asn | Ser | Gly | His 480 |
| Ile | Gln | Ser | Ile | Ile 485 | Asn | Pro | Pro | Gly | Asn 490 | Pro | Lys | Ala | Tyr | Tyr 495 | Leu |
| Ala | Asn | Pro | Lys 500 | Leu | Ser | Ser | Asp | Pro 505 | Arg | Ala | Trp | Leu | His 510 | Asp | Ala |
| Lys | Arg | Ser 515 | Glu | Gly | Ser | Trp | Trp 520 | Pro | Leu | Trp | Leu | Glu 525 | Trp | Ile | Thr |
| Ala | Arg 530 | Ser | Gly | Pro | Leu | Lys 535 | Ala | Pro | Arg | Ser | Glu 540 | Leu | Gly | Asn | Ala |
| Thr 545 | Tyr | Pro | Pro | Leu | Gly 550 | Pro | Ala | Pro | Gly | Thr 555 | Tyr | Val | Leu | Thr | Arg 560 |

( 2 ) INFORMATION FOR SEQ ID NO:12:

( i ) SEQUENCE CHARACTERISTICS:
        ( A ) LENGTH: 590 amino acids
        ( B ) TYPE: amino acid
        ( C ) STRANDEDNESS:
        ( D ) TOPOLOGY: linear ( x i ) SEQUENCE DESCRIPTION: SEQ ID NO:12:

| Met 1 | Asn | Pro | Asn | Ser 5 | Phe | Gln | Phe | Lys | Glu 10 | Asn | Ile | Leu | Gln | Phe 15 | Phe |
| --- | --- | --- | --- | --- | --- | --- | --- | --- | --- | --- | --- | --- | --- | --- | --- |
| Ser | Val | His | Asp 20 | Asp | Ile | Trp | Lys | Lys 25 | Leu | Gln | Glu | Phe | Tyr 30 | Tyr | Gly |
| Gln | Ser | Pro 35 | Ile | Asn | Glu | Ala | Leu 40 | Ala | Gln | Leu | Asn | Lys 45 | Glu | Asp | Met |
| Ser | Leu 50 | Phe | Phe | Glu | Ala | Leu 55 | Ser | Lys | Asn | Pro | Ala 60 | Arg | Met | Met | Glu |
| Met 65 | Gln | Trp | Ser | Trp | Trp 70 | Gln | Gly | Gln | Ile | Gln 75 | Ile | Tyr | Gln | Asn | Val 80 |
| Leu | Met | Arg | Ser | Val | Ala | Lys | Asp | Val | Ala | Pro | Phe | Ile | Gln | Pro | Glu |

|   |   |   |   |   | 85 |   |   |   | 90 |   |   |   | 95 |   |
|---|---|---|---|---|---|---|---|---|---|---|---|---|---|---|
| Ser | Gly | Asp | Arg 100 | Arg | Phe | Asn | Ser | Pro 105 | Leu | Trp | Gln | Glu | His 110 | Pro | Asn |
| Phe | Asp | Leu 115 | Leu | Ser | Gln | Ser | Tyr 120 | Leu | Leu | Phe | Ser | Gln 125 | Leu | Val | Gln |
| Asn | Met 130 | Val | Asp | Val | Val | Glu 135 | Gly | Val | Pro | Asp | Lys 140 | Val | Arg | Tyr | Arg |
| Ile 145 | His | Phe | Phe | Thr | Arg 150 | Gln | Met | Ile | Asn | Ala 155 | Leu | Ser | Pro | Ser | Asn 160 |
| Phe | Leu | Trp | Thr | Asn 165 | Pro | Glu | Val | Ile | Gln 170 | Gln | Thr | Val | Ala | Glu 175 | Gln |
| Gly | Glu | Asn | Leu 180 | Val | Arg | Gly | Met | Gln 185 | Val | Phe | His | Asp | Asp 190 | Val | Met |
| Asn | Ser | Gly 195 | Lys | Tyr | Leu | Ser | Ile 200 | Arg | Met | Val | Asn | Ser 205 | Asp | Ser | Phe |
| Ser | Leu 210 | Gly | Lys | Asp | Leu | Ala 215 | Tyr | Thr | Pro | Gly | Ala 220 | Val | Val | Phe | Glu |
| Asn 225 | Asp | Ile | Phe | Gln | Leu 230 | Leu | Gln | Tyr | Glu | Ala 235 | Thr | Thr | Glu | Asn | Val 240 |
| Tyr | Gln | Thr | Pro | Ile 245 | Leu | Val | Val | Pro | Pro 250 | Phe | Ile | Asn | Lys | Tyr 255 | Tyr |
| Val | Leu | Asp | Leu 260 | Arg | Glu | Gln | Asn | Ser 265 | Leu | Val | Asn | Trp | Leu 270 | Arg | Gln |
| Gln | Gly | His 275 | Thr | Val | Phe | Leu | Met 280 | Ser | Trp | Arg | Asn | Pro 285 | Asn | Ala | Glu |
| Gln | Lys 290 | Glu | Leu | Thr | Phe | Ala 295 | Asp | Leu | Ile | Thr | Gln 300 | Gly | Ser | Val | Glu |
| Ala 305 | Leu | Arg | Val | Ile | Glu 310 | Glu | Ile | Thr | Gly | Glu 315 | Lys | Glu | Ala | Asn | Cys 320 |
| Ile | Gly | Tyr | Cys | Ile 325 | Gly | Gly | Thr | Leu | Leu 330 | Ala | Ala | Thr | Gln | Ala 335 | Tyr |
| Tyr | Val | Ala | Lys 340 | Arg | Leu | Lys | Asn | His 345 | Val | Lys | Ser | Ala | Thr 350 | Tyr | Met |
| Ala | Thr | Ile 355 | Ile | Asp | Phe | Glu | Asn 360 | Pro | Gly | Ser | Leu | Gly 365 | Val | Phe | Ile |
| Asn | Glu 370 | Pro | Val | Val | Ser | Gly 375 | Leu | Glu | Asn | Leu | Asn 380 | Asn | Gln | Leu | Gly |
| Tyr 385 | Phe | Asp | Gly | Arg | Gln 390 | Leu | Ala | Val | Thr | Phe 395 | Ser | Leu | Leu | Arg | Glu 400 |
| Asn | Thr | Leu | Tyr | Trp 405 | Asn | Tyr | Tyr | Ile | Asp 410 | Asn | Tyr | Leu | Lys | Gly 415 | Lys |
| Glu | Pro | Ser | Asp 420 | Phe | Asp | Ile | Leu | Tyr 425 | Trp | Asn | Ser | Asp | Gly 430 | Thr | Asn |
| Ile | Pro | Ala 435 | Lys | Ile | His | Asn | Phe 440 | Leu | Leu | Arg | Asn | Leu 445 | Tyr | Leu | Asn |
| Asn | Glu 450 | Leu | Ile | Ser | Pro | Asn 455 | Ala | Val | Lys | Val | Asn 460 | Gly | Val | Gly | Leu |
| Asn 465 | Leu | Ser | Arg | Val | Lys 470 | Thr | Pro | Ser | Phe | Phe 475 | Ile | Ala | Thr | Gln | Glu 480 |
| Asp | His | Ile | Ala | Leu 485 | Trp | Asp | Thr | Cys | Phe 490 | Arg | Gly | Ala | Asp | Tyr 495 | Leu |
| Gly | Gly | Glu | Ser 500 | Thr | Leu | Val | Leu | Gly 505 | Glu | Ser | Gly | His | Val 510 | Ala | Gly |

```
Ile  Val  Asn  Pro  Pro  Ser  Arg  Asn  Lys  Tyr  Gly  Cys  Tyr  Thr  Asn  Ala
          515                520                525

Ala  Lys  Phe  Glu  Asn  Thr  Lys  Gln  Trp  Leu  Asp  Gly  Ala  Glu  Tyr  His
     530                535                540

Pro  Glu  Ser  Trp  Trp  Leu  Arg  Trp  Gln  Ala  Trp  Val  Thr  Pro  Tyr  Thr
545                550                555                               560

Gly  Glu  Gln  Val  Pro  Ala  Arg  Asn  Leu  Gly  Asn  Ala  Gln  Tyr  Pro  Ser
               565                     570                     575

Ile  Glu  Ala  Ala  Pro  Gly  Arg  Tyr  Val  Leu  Val  Asn  Leu  Phe
               580                585                     590
```

(2) INFORMATION FOR SEQ ID NO:13:

(i) SEQUENCE CHARACTERISTICS:
        (A) LENGTH: 577 amino acids
        (B) TYPE: amino acid
        (C) STRANDEDNESS:
        (D) TOPOLOGY: linear (xi) SEQUENCE DESCRIPTION: SEQ ID NO:13:

```
Met  Ala  Arg  Ala  Ala  Glu  Gln  Leu  Gly  Lys  Ala  Ala  Ser  Ala  Trp  Leu
1                   5                   10                  15

Ala  Pro  Arg  Glu  Ala  Gly  Glu  Lys  Thr  Asp  Ser  Phe  Ala  Glu  Pro  Val
               20                  25                  30

Ser  Asp  Met  Val  Lys  Thr  Leu  Ser  Lys  Val  Ser  Glu  Tyr  Trp  Leu  Ser
          35                  40                  45

Asp  Pro  Arg  Arg  Thr  Leu  Glu  Ala  Gln  Thr  His  Leu  Leu  Gly  Ser  Phe
     50                  55                  60

Phe  Asp  Met  Trp  Ser  Arg  Thr  Leu  Gln  Arg  Met  Ala  Ala  Asp  Ala  Val
65                  70                  75                            80

Glu  Asp  Pro  Ala  Asn  Leu  Gln  His  Asn  Asp  Lys  Arg  Phe  Ala  Asp  Glu
               85                  90                       95

Asp  Trp  Val  Lys  Asn  Pro  Phe  Phe  Asp  Phe  Ile  Arg  Gln  Ala  Tyr  Phe
               100                 105                 110

Val  Thr  Ser  Asp  Trp  Ala  Glu  Arg  Met  Val  Lys  Asp  Ala  Glu  Gly  Leu
          115                 120                 125

Asp  Asp  His  Thr  Arg  His  Lys  Ala  Ala  Phe  Tyr  Val  Arg  Gln  Ile  Ala
          130                 135                 140

Ser  Ala  Leu  Ser  Pro  Thr  Asn  Phe  Ile  Thr  Thr  Asn  Pro  Gln  Leu  Tyr
145                 150                 155                           160

Arg  Glu  Thr  Val  Ala  Ser  Ser  Gly  Ala  Asn  Leu  Val  Lys  Gly  Met  Gln
               165                 170                 175

Met  Leu  Ala  Glu  Asp  Ile  Ala  Ala  Gly  Arg  Gly  Glu  Leu  Arg  Leu  Arg
               180                 185                 190

Gln  Thr  Asp  Thr  Ser  Lys  Phe  Ala  Ile  Gly  Glu  Asn  Ile  Ala  Ile  Thr
          195                 200                 205

Pro  Gly  Lys  Val  Ile  Ala  Gln  Asn  Asp  Val  Cys  Gln  Val  Leu  Gln  Tyr
     210                 215                 220

Glu  Ala  Ser  Thr  Glu  Thr  Val  Leu  Lys  Arg  Pro  Leu  Leu  Ile  Cys  Pro
225                 230                 235                           240

Pro  Trp  Ile  Asn  Lys  Phe  Tyr  Val  Leu  Asp  Leu  Asn  Pro  Glu  Lys  Ser
               245                 250                 255

Phe  Ile  Lys  Trp  Ala  Val  Asp  Gln  Gly  Gln  Thr  Val  Phe  Val  Ile  Ser
               260                 265                 270

Trp  Val  Asn  Pro  Asp  Glu  Arg  His  Ala  Ser  Lys  Asp  Trp  Glu  Ala  Tyr
          275                 280                 285
```

```
Ala  Arg  Glu  Gly  Ile  Gly  Phe  Ala  Leu  Asp  Ile  Ile  Glu  Gln  Ala  Thr
     290                 295                 300
Gly  Glu  Arg  Glu  Val  Asn  Ser  Ile  Gly  Tyr  Cys  Val  Gly  Gly  Thr  Leu
305                      310                 315                           320
Leu  Ala  Ala  Thr  Leu  Ala  Leu  His  Ala  Ala  Glu  Gly  Asp  Glu  Arg  Ile
               325                      330                           335
Arg  Ser  Ala  Thr  Leu  Phe  Thr  Thr  Gln  Val  Asp  Phe  Thr  His  Ala  Gly
               340                 345                      350
Asp  Leu  Lys  Val  Phe  Val  Asp  Asp  Gln  Ile  Arg  His  Leu  Glu  Ala
          355                      360                 365
Asn  Met  Ser  Ala  Thr  Gly  Tyr  Leu  Glu  Gly  Ser  Lys  Met  Ala  Ser  Ala
     370                      375                 380
Phe  Asn  Met  Leu  Arg  Ala  Ser  Glu  Leu  Ile  Trp  Pro  Tyr  Phe  Val  Asn
385                      390                 395                           400
Asn  Tyr  Leu  Lys  Gly  Gln  Asp  Pro  Leu  Pro  Phe  Asp  Leu  Leu  Tyr  Trp
               405                 410                      415
Asn  Ser  Asp  Ser  Thr  Arg  Met  Pro  Ala  Ala  Asn  His  Ser  Phe  Tyr  Leu
               420                 425                      430
Arg  Asn  Cys  Tyr  Leu  Glu  Asn  Arg  Leu  Ser  Arg  Gly  Glu  Met  Met  Leu
          435                      440                 445
Ala  Gly  Arg  Arg  Val  Ser  Leu  Gly  Asp  Val  Lys  Ile  Pro  Ile  Tyr  Asn
     450                      455                 460
Leu  Ala  Thr  Lys  Glu  Asp  His  Ile  Ala  Pro  Ala  Lys  Ser  Val  Phe  Leu
465                      470                 475                           480
Gly  Ser  Ser  Ser  Phe  Gly  Gly  Lys  Val  Thr  Phe  Val  Leu  Ser  Gly  Ser
               485                 490                      495
Gly  His  Ile  Ala  Gly  Val  Val  Asn  Pro  Pro  Ala  Arg  Ser  Lys  Tyr  Gln
               500                 505                      510
Tyr  Trp  Thr  Gly  Gly  Ala  Pro  Lys  Gly  Asp  Ile  Glu  Thr  Trp  Met  Gly
          515                      520                 525
Lys  Ala  Lys  Glu  Thr  Ala  Gly  Ser  Trp  Trp  Pro  His  Trp  Gln  Gly  Trp
     530                      535                 540
Val  Glu  Arg  Leu  Asp  Lys  Arg  Arg  Val  Pro  Ala  Arg  Lys  Ala  Gly  Gly
545                      550                 555                           560
Pro  Leu  Asn  Ser  Ile  Glu  Glu  Ala  Pro  Gly  Ser  Tyr  Val  Arg  Val  Arg
               565                 570                      575
Ala
```

( 2 ) INFORMATION FOR SEQ ID NO:14:

( i ) SEQUENCE CHARACTERISTICS:
        ( A ) LENGTH: 561 amino acids
        ( B ) TYPE: amino acid
        ( C ) STRANDEDNESS:
        ( D ) TOPOLOGY: linear ( x i ) SEQUENCE DESCRIPTION: SEQ ID NO:14:

```
Leu  Asp  His  Val  His  Lys  Lys  Leu  Lys  Ser  Thr  Leu  Asp  Pro  Ile  Gly
1                   5                    10                       15
Trp  Gly  Pro  Ala  Val  Thr  Ser  Val  Ala  Gly  Arg  Ala  Val  Arg  Asn  Pro
               20                  25                       30
Gln  Ala  Val  Thr  Ala  Ala  Thr  Ala  Glu  Tyr  Ala  Gly  Arg  Leu  Ala  Lys
               35                  40                       45
Ile  Pro  Ala  Ala  Ala  Thr  Arg  Val  Phe  Asn  Ala  Asn  Asp  Pro  Asp  Ala
          50                       55                  60
Pro  Met  Pro  Val  Asp  Pro  Arg  Asp  Arg  Arg  Phe  Ser  Asp  Thr  Ala  Trp
```

```
 65                          70                         75                         80
Gln  Glu  Asn  Pro  Ala  Tyr  Phe  Ser  Leu  Leu  Gln  Ser  Tyr  Leu  Ala  Thr
                    85                       90                       95
Arg  Ala  Tyr  Val  Glu  Glu  Leu  Thr  Glu  Ala  Gly  Ser  Gly  Asp  Pro  Leu
               100                      105                      110
Gln  Asp  Gly  Lys  Ala  Arg  Gln  Phe  Ala  Asn  Leu  Met  Phe  Asp  Ala  Leu
          115                      120                      125
Ala  Pro  Ser  Asn  Phe  Leu  Trp  Asn  Pro  Gly  Val  Leu  Thr  Arg  Ala  Phe
     130                      135                      140
Glu  Thr  Gly  Gly  Ala  Ser  Leu  Leu  Arg  Gly  Ala  Arg  Tyr  Ala  Ala  His
145                      150                      155                      160
Asp  Ile  Leu  Asn  Arg  Gly  Gly  Leu  Pro  Leu  Lys  Val  Asp  Ser  Asp  Ala
                    165                      170                      175
Phe  Thr  Val  Gly  Glu  Asn  Leu  Ala  Ala  Thr  Pro  Gly  Lys  Val  Val  Phe
               180                      185                      190
Arg  Asn  Asp  Leu  Ile  Glu  Leu  Ile  Gln  Tyr  Ala  Pro  Gln  Thr  Glu  Gln
          195                      200                      205
Val  His  Ala  Val  Pro  Ile  Leu  Ala  Ala  Pro  Pro  Trp  Ile  Asn  Lys  Tyr
     210                      215                      220
Tyr  Ile  Leu  Asp  Leu  Ala  Pro  Gly  Arg  Ser  Leu  Ala  Glu  Trp  Ala  Val
225                      230                      235                      240
Gln  His  Gly  Arg  Thr  Val  Phe  Met  Ile  Ser  Tyr  Arg  Asn  Pro  Asp  Glu
                    245                      250                      255
Ser  Met  Arg  His  Ile  Thr  Met  Asp  Asp  Tyr  Tyr  Val  Asp  Gly  Ile  Ala
               260                      265                      270
Thr  Ala  Leu  Asp  Val  Val  Glu  Glu  Ile  Thr  Gly  Ser  Pro  Lys  Ile  Glu
          275                      280                      285
Val  Leu  Ser  Ile  Cys  Leu  Gly  Gly  Ala  Met  Ala  Ala  Met  Ala  Ala  Ala
     290                      295                      300
Arg  Ala  Phe  Ala  Val  Gly  Asp  Lys  Arg  Val  Ser  Ala  Phe  Thr  Met  Leu
305                      310                      315                      320
Asn  Thr  Leu  Leu  Asp  Tyr  Ser  Gln  Val  Gly  Glu  Leu  Gly  Leu  Leu  Thr
                    325                      330                      335
Asp  Pro  Ala  Thr  Leu  Asp  Leu  Val  Glu  Phe  Arg  Met  Arg  Gln  Gln  Gly
               340                      345                      350
Phe  Leu  Ser  Gly  Lys  Glu  Met  Ala  Gly  Ser  Phe  Asp  Met  Ile  Arg  Ala
          355                      360                      365
Lys  Asp  Leu  Val  Phe  Asn  Tyr  Trp  Val  Ser  Arg  Trp  Met  Lys  Gly  Glu
     370                      375                      380
Lys  Pro  Ala  Ala  Phe  Asp  Ile  Leu  Ala  Trp  Asn  Glu  Asp  Ser  Thr  Ser
385                      390                      395                      400
Met  Pro  Ala  Glu  Met  His  Ser  His  Tyr  Leu  Arg  Ser  Leu  Tyr  Gly  Arg
                    405                      410                      415
Asn  Glu  Leu  Ala  Glu  Gly  Leu  Tyr  Val  Leu  Asp  Gly  Gln  Pro  Leu  Asn
               420                      425                      430
Leu  His  Asp  Ile  Ala  Cys  Asp  Thr  Tyr  Val  Val  Gly  Ala  Ile  Asn  Asp
          435                      440                      445
His  Ile  Val  Pro  Trp  Thr  Ser  Ser  Tyr  Gln  Ala  Val  Asn  Leu  Leu  Gly
     450                      455                      460
Gly  Asp  Val  Arg  Tyr  Val  Leu  Thr  Asn  Gly  Gly  His  Val  Ala  Gly  Ala
465                      470                      475                      480
Val  Asn  Pro  Pro  Gly  Lys  Arg  Val  Trp  Phe  Lys  Ala  Val  Gly  Ala  Pro
                    485                      490                      495
```

5,849,894

| | | | | | | | | | | | | | | | |
|---|---|---|---|---|---|---|---|---|---|---|---|---|---|---|---|
| Asp | Ala | Glu | Ser | Gly | Thr | Pro | Leu | Pro | Ala | Asp | Pro | Gln | Val | Trp | Asp |
| | | | 500 | | | | 505 | | | | | 510 | | | |
| Glu | Ala | Ala | Thr | Arg | Tyr | Glu | His | Ser | Trp | Trp | Glu | Asp | Trp | Thr | Ala |
| | | 515 | | | | | 520 | | | | | 525 | | | |
| Trp | Ser | Asn | Lys | Arg | Ala | Gly | Glu | Leu | Val | Ala | Pro | Ala | Met | Gly | |
| 530 | | | | | | 535 | | | | | 540 | | | | |
| Ser | Thr | Ala | His | Pro | Pro | Leu | Glu | Asp | Ala | Pro | Gly | Thr | Tyr | Val | Phe |
| 545 | | | | | 550 | | | | | 555 | | | | | 560 |
| Ser | | | | | | | | | | | | | | | |

( 2 ) INFORMATION FOR SEQ ID NO:15:

( i ) SEQUENCE CHARACTERISTICS:
            ( A ) LENGTH: 601 amino acids
            ( B ) TYPE: amino acid
            ( C ) STRANDEDNESS:
            ( D ) TOPOLOGY: linear ( x i ) SEQUENCE DESCRIPTION: SEQ ID NO:15:

| | | | | | | | | | | | | | | | |
|---|---|---|---|---|---|---|---|---|---|---|---|---|---|---|---|
| Met | Ala | Thr | Glu | Glu | Gln | Ser | Pro | Gly | Ser | Gly | Arg | Asp | Ala | Gln | Phe |
| 1 | | | | 5 | | | | | 10 | | | | | 15 | |
| Glu | Arg | Leu | Asn | Ala | Asn | Leu | Thr | Arg | Ile | Asp | Glu | Leu | Ser | Lys | Arg |
| | | | 20 | | | | 25 | | | | | 30 | | | |
| Leu | Thr | Ala | Ala | Leu | Thr | Lys | Arg | Lys | Leu | Ser | Asp | Pro | Ala | Leu | His |
| | | 35 | | | | 40 | | | | | 45 | | | | |
| Gly | Pro | Ser | Gly | Asp | Val | Phe | Leu | Lys | Ala | Met | Thr | Ala | Tyr | Met | Ala |
| | 50 | | | | 55 | | | | | 60 | | | | | |
| Glu | Met | Met | Gln | Asn | Pro | Ala | Lys | Ile | Leu | Glu | His | Gln | Ile | Ser | Phe |
| 65 | | | | | 70 | | | | 75 | | | | | | 80 |
| Trp | Gly | Lys | Ser | Leu | Lys | His | Tyr | Val | Glu | Ala | Gln | His | Gln | Leu | Val |
| | | | | 85 | | | | | 90 | | | | | 95 | |
| Lys | Gly | Glu | Leu | Lys | Pro | Pro | Pro | Asp | Val | Thr | Pro | Lys | Asp | Arg | Arg |
| | | | 100 | | | | | 105 | | | | 110 | | | |
| Phe | Ser | Asn | Pro | Leu | Trp | Gln | Thr | His | Pro | Phe | Phe | Asn | Tyr | Leu | Lys |
| | | 115 | | | | | 120 | | | | | 125 | | | |
| Gln | Gln | Tyr | Leu | Met | Asn | Ala | Glu | Ala | Val | Asn | Gln | Ala | Val | Glu | Gly |
| | 130 | | | | | 135 | | | | | 140 | | | | |
| Leu | Glu | His | Ile | Glu | Pro | Ser | Asp | Lys | Lys | Arg | Val | Glu | Tyr | Phe | Ser |
| 145 | | | | | 150 | | | | | 155 | | | | | 160 |
| Arg | Gln | Ile | Val | Asp | Leu | Phe | Ser | Pro | Thr | Asn | Phe | Phe | Gly | Thr | Asn |
| | | | | 165 | | | | | 170 | | | | | 175 | |
| Pro | Asp | Ala | Leu | Glu | Arg | Ala | Ile | Ala | Thr | Asp | Gly | Glu | Ser | Leu | Val |
| | | | 180 | | | | | 185 | | | | 190 | | | |
| Gln | Gly | Leu | Glu | Asn | Leu | Val | Arg | Asp | Ile | Glu | Ala | Asn | Asn | Gly | Asp |
| | | 195 | | | | | 200 | | | | | 205 | | | |
| Leu | Leu | Val | Thr | Leu | Ala | Asp | Pro | Glu | Ala | Phe | Gln | Val | Gly | Gln | Asn |
| | 210 | | | | | 215 | | | | | 220 | | | | |
| Leu | Ala | Thr | Thr | Glu | Gly | Ser | Val | Val | Tyr | Arg | Asn | Arg | Met | Phe | Glu |
| 225 | | | | | 230 | | | | | 235 | | | | | 240 |
| Leu | Ile | Gln | Tyr | Lys | Pro | Thr | Thr | Glu | Thr | Val | His | Glu | Thr | Pro | Leu |
| | | | | 245 | | | | | 250 | | | | | 255 | |
| Leu | Ile | Phe | Pro | Pro | Trp | Ile | Asn | Lys | Phe | Tyr | Ile | Leu | Asp | Leu | Lys |
| | | | 260 | | | | | 265 | | | | | 270 | | |
| Pro | Gln | Asn | Ser | Leu | Leu | Lys | Trp | Leu | Val | Asp | Gln | Gly | Phe | Thr | Val |
| | | 275 | | | | | 280 | | | | | 285 | | | |
| Phe | Val | Val | Ser | Trp | Val | Asn | Pro | Asp | Lys | Ser | Tyr | Ala | Gly | Ile | Gly |

|  |  |  |  |  | 290 |  |  |  |  | 295 |  |  |  |  | 300 |  |
|---|---|---|---|---|---|---|---|---|---|---|---|---|---|---|---|---|
| Met 305 | Asp | Asp | Tyr | Ile | Arg 310 | Glu | Gly | Tyr | Met | Arg 315 | Ala | Met | Ala | Glu | Val 320 |
| Arg | Ser | Ile | Thr | Arg 325 | Gln | Lys | Gln | Ile | Asn 330 | Ala | Val | Gly | Tyr | Cys 335 | Ile |
| Ala | Gly | Thr | Thr 340 | Leu | Thr | Leu | Thr | Leu 345 | Ala | His | Leu | Gln | Lys 350 | Ala | Gly |
| Asp | Pro | Ser 355 | Val | Arg | Ser | Ala | Thr 360 | Phe | Phe | Thr | Thr | Leu 365 | Thr | Asp | Phe |
| Ser | Asp 370 | Pro | Gly | Glu | Val | Gly 375 | Val | Phe | Leu | Asn | Asp 380 | Asp | Phe | Val | Asp |
| Gly 385 | Ile | Glu | Arg | Gln | Val 390 | Ala | Val | Asp | Gly | Ile 395 | Leu | Asp | Lys | Thr | Phe 400 |
| Met | Ser | Arg | Thr | Phe 405 | Ser | Tyr | Leu | Arg | Ser 410 | Asn | Asp | Leu | Ile | Tyr 415 | Gln |
| Pro | Ala | Ile | Lys 420 | Ser | Tyr | Met | Met | Gly 425 | Glu | Ala | Pro | Pro | Ala 430 | Phe | Asp |
| Leu | Leu | Tyr 435 | Trp | Asn | Gly | Asp | Gly 440 | Thr | Asn | Leu | Pro | Ala 445 | Gln | Met | Ala |
| Val | Glu 450 | Tyr | Leu | Arg | Gly | Leu 455 | Cys | Gln | Gln | Asp | Arg 460 | Leu | Ala | Gly | Gly |
| Thr 465 | Phe | Pro | Val | Leu | Gly 470 | Ser | Pro | Val | Gly | Leu 475 | Lys | Asp | Val | Thr | Leu 480 |
| Pro | Val | Cys | Ala | Ile 485 | Ala | Cys | Glu | Thr | Asp 490 | His | Ile | Ala | Pro | Trp 495 | Lys |
| Ser | Ser | Phe | Asn 500 | Gly | Phe | Arg | Gln | Phe 505 | Gly | Ser | Thr | Asp | Lys 510 | Thr | Phe |
| Ile | Leu | Ser 515 | Gln | Ser | Gly | His | Val 520 | Ala | Gly | Ile | Val | Asn 525 | Pro | Pro | Ser |
| Arg | Asn 530 | Lys | Tyr | Gly | His | Tyr 535 | Thr | Asn | Glu | Gly | Pro 540 | Ala | Gly | Thr | Pro |
| Glu 545 | Ser | Phe | Arg | Glu | Gly 550 | Ala | Glu | Phe | His | Ala 555 | Gly | Ser | Trp | Trp | Pro 560 |
| Arg | Trp | Gly | Ala | Trp 565 | Leu | Ala | Glu | Arg | Ser 570 | Gly | Lys | Gln | Val | Pro 575 | Ala |
| Arg | Gln | Pro | Gly 580 | Asp | Ser | Lys | His | Pro 585 | Glu | Leu | Ala | Pro | Ala 590 | Pro | Gly |
| Ser | Tyr | Val 595 | Ala | Ala | Val | Gly | Gly 600 | Ala |  |  |  |  |  |  |  |

RHODOSPIRILLUM RUBRUM POLY-β-HYDROXYALKANOATE SYNTHASE

This application claims the benefit of provisional application Ser. No. 60/007,693, filed Nov. 29, 1995.

BACKGROUND OF THE INVENTION

1. Field of the Invention

The present invention relates to poly-β-hydroxyalkanoate (PHA) synthases, such as that from *Rhodospirillum rubrum*, which exhibit flexible substrate specificity. These synthases can be expressed in transformed microorganisms and plants to produce poly-β-hydroxyalkanoates (PHAS) possessing varied physical properties depending upon the monomers incorporated therein.

2. Description of Related Art

The production of intracellular polyesters belonging to the class of polymers known as poly-β-hydroxyalkanoates (PHAs) has been observed in a wide array of prokaryotic organisms (Anderson and Dawes (1990) *Microbiol. Rev.* 54:450). The monomers composing the polyesters range in length from C4 (β-hydroxybutyrate) to C12 (β-hydroxydodecanoate) (Lageveen et al. (1988) *Appl. Env. Microbiol.* 54:2924). This class of polyesters has attracted much attention as a potential alternative to conventional petrochemical-derived plastics.

PHAs are broadly characterized according to the monomers that constitute their backbone. Polymers composed of C4-C5 units are classified as short chain length (scl) PHAs; polymers containing monomers of C6 units and above are classified as medium chain length (mcl) PHAs. The primary structure of the polymer influences the physical properties of the polyester.

The metabolic pathways leading to the formation of PHAs have not been elucidated for all organisms. The most extensively studied PHA biosynthetic pathway is that of *Alcaligenes eutrophus* (Peoples et al. (1989) *J. Biol. Chem.* 264:15298 and Valentin et. al. (1995) *Eur. J. Biochem.* 227:43). This organism is capable of forming either a homopolymer of C4 (polyhydroxybutyrate, PHB) or a co-polymer of C4-C5 (PHB-PHV, polyhydroxybutyrate-polyhydroxyvalerate) (Koyama and Doi (1995) *Biotechnol. Lett.* 17:281). Hence, *A. eutrophus* is classified as a scl PHA organism. Similarly, Pseudomonas species generate a polymer composed of monomers ranging in length from C6 to C12 (Timm and Steinbüchel (1990) *Appl. Environ. Microbiol.* 56:3360 and Lageveen et al. (1988) *Appl. Environ. Microbiol.* 54:2924), and are classified as mcl PHA organisms.

The polymerization of the D-3-hydroxyacyl-CoA substrates is carried out by PHA synthases. The substrate specificity of this class of enzyme varies across the spectrum of PHA producing organisms. This variation in substrate specificity of PHA synthases is supported by indirect evidence observed in heterologous expression studies (Lee et al. (1995) *Appl. Microbiol. Biotechnol.* 42:901 and Timm et al. (1990) *Appl. Microbiol. Biotech.* 33:296). Hence, the structure of the backbone of the polymer is strongly influenced by the PHA synthase responsible for its formation.

The phototrophic, purple, non-sulphur bacterium *Rhodospirillum rubrum* (ATCC 25903) is capable of accumulating PHA (Anderson and Dawes (1990) *Microbiol. Rev.* 54:450 and Brandl et al. (1989) *Inter. J. Biol. Macromol.* 11:49). The PHA synthase from this strain of Rhodospirillum is quite promiscuous, based on the PHA co-polymers it is capable of generating when fermented with a diverse range of carbon substrates under PHA-accumulating conducive conditions (Brandl et al., supra, and Ulmer et al. (1994) *Macromolecules* 27:1675).

SUMMARY OF THE INVENTION

The present invention provides an isolated DNA fragment comprising a nucleotide sequence encoding an enzyme having *Rhodospirillum rubrum* PHA synthase enzymatic activity. This fragment comprises a PHA synthase gene from *Rhodospirillum rubrum* (ATCC 25903) encoding an enzyme possessing flexible substrate specificity. This gene and the PHA synthase encoded thereby, as well as biologically functional equivalents thereof, respectively, can be used in the production of novel co-polymers of PHA in both prokaryotic and eukaryotic organisms, including plants. Transformed bacteria and transgenic plants comprising and expressing this gene or its equivalents will be able to polymerize both 3-hydroxy-acyl-ACP and/or 3-hydroxyacyl-CoA substrates, and thereby produce novel biodegradative polyesters having physical properties similar to those of petrochemical-derived plastics.

Further scope of the applicability of the present invention will become apparent from the detailed description provided below. However, it should be understood that the following detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only and are not limitative of the present invention, in which.

SEQ ID NOS:1–15 depict the following

Figure 1:
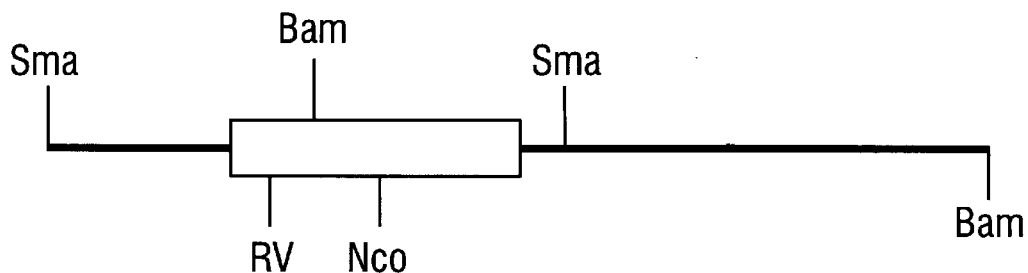
FIG. 1 shows a partial restriction map of the two genomic subclones derived from the 21–23 kb Eco RI genomic fragment harboring the PHA synthase from *R. rubrum*. The open reading frame (ORF) of the PHA synthase from *R. rubrum* is indicated by an open box. The 3.0 kb Sma I subclone resides in pMON 25657 (FIG. 2) and carries the entire ORF. The 6.5 kb Bam HI fragment residing in pMON 25658 (FIG. 3) is missing the 5' region of the PHA synthase ORF, but contains additional sequence beyond the 3' end. RV: EcoRV.

SEQ ID NO:1 shows the nucleotide sequences of the coding and non-coding strands of the PHA synthase-encoding DNA fragment from *R. rubrum* (ATCC 25903), as well as the deduced amino acid sequence.

SEQ ID NO:2 shows the deduced amino acid sequence of the *R. rubrum* PHA synthase encoded by SEQ ID NO:1 when the ATG at nucleotide positions 8–10 is the translational initiation start site.

SEQ ID NO:3 shows the deduced amino acid sequence of the *R. rubrum* PHA synthase encoded by SEQ ID NO:1 when the ATG at nucleotide positions 122–124 is the translational initiation start site.

SEQ ID NO:4 shows the deduced amino acid sequence of the *R. rubrum* PHA synthase encoded by SEQ ID NO:1 when the ATG at nucleotide positions 200–202 is the translational initiation start site.

SEQ ID NOS:5–15 show the amino acid sequences of the PHA synthases from the following 11 microorganisms:

SEQ ID NO:5: *Alcaligenes eutrophus*
SEQ ID NO:6: *Methylobacterium extorquens*
SEQ ID NO:7: *Pseudomonas aeruginosa* (synthase 1)
SEQ ID NO:8: *Pseudomonas aeruginosa* (synthase 2)
SEQ ID NO:9: *Paracoccus denitrificans*
SEQ ID NO:10: *Pseudomonas oleovorans* (synthase 1)
SEQ ID NO:11: *Pseudomonas oleovorans* (synthase 2)
SEQ ID NO:12: *Acinetobacter sp.* RA3849
SEQ ID NO:13: *Rhizobium meliloti*
SEQ ID NO:14: *Rhodococcus ruber*
SEQ ID NO:15: *Rhodobacter sphaeroides*

Organisms included in the sequence listing include *P. denitrifificans* (*Paracoccus denitrificans*, unpublished, accession D43764); *R. sphaeroides* (*Rhodobacter sphaeroides*, Hustede and Steinbüchel (1993) *Biotechnol. Lett.* 15:709, accession L17049); *M. extorquens* (*Methylobacteriumextorquens*, Hustede and Steinbüchel (1993), supra, accession L07893); *R. meliloti* (*Rhizobium meliloti*, unpublished, accession U17227); *R. rubrum* (*Rhodospirillum rubrum*, ATCC 25903); Acinetobacter (*Acinetobacter sp.* RA3849, Schembri et al. (1994) *FEMS Microbiol. Lett.* 118:145, accession U04848); *A. eutrophus* (*Alcaligenes eutrophus*, Peoples and Sinskey (1989) *J. Biol. Chem.* 264:15298, accession J05003); *P. aeruginosa*-1 (*Pseudomonas aeruginosa* (synthase 1), Timm and Steinbüchel (1992) *Eur. J. Biochem.* 209:15, accession S29305); *P. oleovorans*-1 (*Pseudomonas oleovorans* (synthase 1), Huisman et al. (1991) *J. Biol. Chem.* 266:2191, accession number M58445); *P. aeruginosa*-2 (*P. aeruginosa* (synthase 2), Timm and Steinbüchel 1992, supra, accession S28379); *P. oleovorans*-2 (*Pseudomonas oleovorans* (synthase 2), Huisman et al. 1991, supra, accession number M58445); and *R. ruber* (*Rhodococcus ruber*, Pieper and Steinbüchel (1992) *FEMS Microbiol. Lett.* 96:73, accession S25725).

DETAILED DESCRIPTION OF THE INVENTION

The following detailed description is provided to aid those skilled in the art in practicing the present invention. Even so, the following detailed description should not be construed to unduly limit the present invention as modifications and variations in the embodiments herein discussed can be made by those of ordinary skill in the art without departing from the spirit or scope of the present inventive discovery.

The contents of each of the references cited herein, including the contents of each of the references cited within each of these references, are herein incorporated by reference in their entirety.

The polymerization of 3-hydroxyacyl-CoA substrates to produce the class of polyesters known as PHAs within prokaryotic cells is catalyzed by PHA synthases. PHA synthases tend to possess inherent substrate specificities that restrict an organism to producing either scl or mcl PHAs. A subset of prokaryotic organisms has been identified that are capable of generating PHAs from monomers having chain lengths that span the classifications scl/mcl. These include species within the genera Nocardia, Pseudomonas, Thiocapsa, Chromatium, Aeromonas, Rhodococcus, and Rhodospirillum. Isolation and characterization of the PHA synthase from a representative of this class of PHA producing organisms provides a means of generating PHAs that possess unique physical properties in heterologous prokaryotic and eukaryotic systems. In the present invention, the PHA synthase from *R. rubrum* (ATCC 25903) was targeted as a representative synthase from this class of PHA producing organisms.

The genes required for the production of PHA within *A. eutrophus* have been cloned and sequenced (Schubert et al. (1988) *J. Bacteriol.* 170:5837). These include phbA, phbB, andphbC, encoding β-ketothiolase, acetoacetyl-CoA reductase, and PHB synthase, respectively. At the protein level, there are known conserved amino acid residues that serve as hallmarks for PHA synthases (Peoples and Sinskey (1989) *J. Biol. Chem.* 264:15298; FIGS. 4A–4E). Under conditions of low stringency, the PHA synthase from *A. eztrophus* can be used as a heterologous probe to screen genomic libraries to identify PHA synthases from other organisms (Timm and Steinbüchel (1992) *Eur. J. Biochem.* 209:15; Valentin and Steinbüchel (1992) *Appl. Microbiol. Biotechnol.* 39:309; Liebergesell et al. (1993) *Appl. Microbiol. Biotechnol.* 40:292).

As described below, an Eco RI partial genomic library of *R. rubrum* (ATCC 25903) was constructed in λ Dash II® (Stratagene, Catalogue No. 247212), and positive plaques were isolated and further characterized. These results are described in Example 2. A hybridizing signal was localized on an approximately 21–23 kb Eco RI fragment. The hybridizing signal was further localized to a 6.5 kb Bam HI fragment and a 3.0 kb Sma I fragment from within the approximately 21–23 kb Eco RI fragment. The 6.5 kb Bam HI and 3.0 kb Sma I fragments were subsequently subcloned into pSP72 (Promega, Catalogue No. P2191). These results are described in Example 3.

Figure 2:
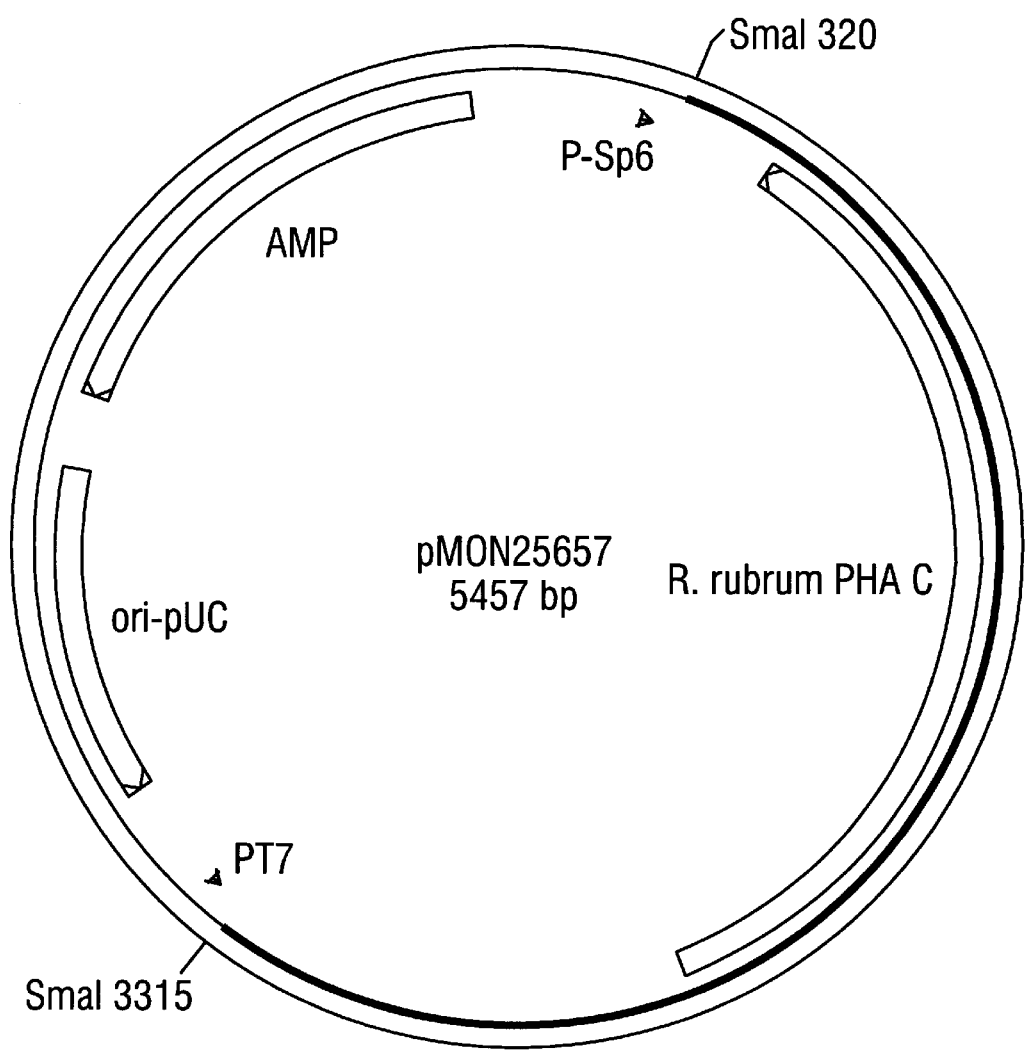
FIG. 2 is a map of pMON 25657. The solid black line represents the 3.0 kb Sma I subclone containing the entire *R. rubrum* PHA synthase ORF within this plasmid. The open box corresponding to *R. rubrum* PHA C shows the coding region for the *R. rubrum* PHA synthase. PT7: promoter element for T7 RNA polymerase; P-Sp6: promoter element for Sp6 RNA polymerase.

The 3.0 kb Sma I fragment subcloned into pSP72 was designated pMON 25657 (FIG. 2). The ORF of the PHA synthase resided within the 3.0 kb Sma I fragment.

Analysis of the activity of this flexible PHA synthase from *R. rubrum* (ATCC 25903) in heterologous systems will facilitate the identification of subdomains within the ORF that are responsible for substrate specificities across this third class of PHA synthases that are capable of incorporating both scl and mcl monomers into polyesters.

EXAMPLE 1

In Vivo Biosynthetic Activity of the PHA Synthase From *R. Rubrum* (ATCC 25903) With Various Substrates Table 1 shows the composition of PHA polymer accumulated by *R. rubrum* (ATCC 25903) after 5 days of growth followed by 10 days under PHA-synthetic conducive conditions. Fermentation with the various carbon sources and analysis of the methyl esters were conducted as described by Brandl et al. ((1989) *Inter. J. Biol. Macromol.* 11:49). The %

PHA column shows the percentage of the dry weight of the cells attributable to polymer. The % MOL column shows the percent molar ratio of the methyl esters of the C4 3-hydroxybutyrate (3HB), the C5 3-hydroxyvalerate (3HV), and the C6 3-hydroxyhexanoate (3HH), respectively, in the accumulated PHA.

TABLE 1

Polymer composition of *R. rubrum* (ATCC 25903) after 5 days growth followed by 10 days under PHA-synthetic conducive conditions

| Evaluated Carbon Source | Dry Wt of Cells | % PHA | % MOL 3HB | 3HB | 3HH |
|---|---|---|---|---|---|
| 0.10% Caproic Acid | 360 mg | 2.6 | 76 | 4 | 20 |
| 0.02% 3-octanoic | 700 mg | 0.3 | 60 | 40 | trace |
| 0.04% 3-hexanoic | 480 mg | 5.0 | 67 | 9 | 24 |

These results show that the PHA synthase from *R. rubrum* (ATCC 25903) is capable of incorporating both scl and mcl monomers into a copolymer. This enzyme was therefore targeted as representative of the synthases from the subset of organisms that have been identified as having such biosynthetically flexible synthases.

EXAMPLE 2

Cloning of a DNA Fragnent From *R. rubrum* (ATCC 25903) Encoding PHA Synthase

Molecular biological techniques routinely employed in the art are described, for example, in Sambrook et al., *Molecular Cloning A, Laboratory Manual*, Second Edition, 1989, Cold Spring Harbor Laboratory Press, Cold Spring Harbor, N.Y., and Ausubel et al., *Current Protocols in Molecular Biology*, 1995, John Wiley & Sons, Inc. The PHA synthase-encoding DNA of *R. rubrum* (ATCC 25903) was isolated from a partial Eco RI genomic library using such techniques as described below.

Growth and Harvesting of Bacteria

*R. rubrum* (ATCC 25903) was grown anaerobically under illumination (60 watt incandescent bulb) at 30° C. in R 8 A H medium (ATCC *Catalogue of Bacteria and Bacteriophages*, 18th edition, 1992, p. 435). Five 25 ml cultures were grown for 5 days. Cultures were subsequently centrifuged at 5,000 rpm for 10 min. to pellet the cells.

Bacterial Lysis and Extraction of DNA

The bacterial pellet obtained from 100 mls of culture was resuspended in 10 mls cell lysis solution composed of 50 mM glucose, 10 mM EDTA (pH 8.0), 25 mM Tris HCl (pH 8.0), 2 mg/ml lysozyme, and 1% SDS. This suspension was frozen on dry ice for 15 min. and placed at 70° C. in a water bath for 10 min. This freeze/heat step was repeated two additional times to lyse the cells.

Lysed cells were extracted four times in phenol/ chloroform/ isoamyl alcohol, 25:24:1, v/v/v. Nucleic acids were subsequently precipitated by the addition of 2× volume of cold absolute ethanol. The resulting pellet was resuspended in 5 ml TE (10:1, pH 8.0) buffer. The resultant solution was dialyzed overnight against 2 liters TE (10:1, pH 8.0) buffer at 4° C. The dialyzed solution was treated with 3 μof RNAase (10 mg/ml) for 30 min. at 37° C. The DNA was precipitated with 0.1 vol of 3.0M sodium acetate and 2 volumes absolute ethanol. The resultant pellet was resuspended in 1 ml TE ( 10:1, pH 8.0) buffer.

Digestion and Cloning of Genomic DNA

Genomic DNA was digested with Eco RI (Boehringer) according to the manufacturer's instructions at 37° C. for 15, 30, and 45 min., and fragments ranging in size from 15–23 kb were purified from 0.8% low melting point agarose gel by a series of phenol/chloroform extractions.

The purified Eco RI fragments of *R. rubrum* genomic DNA were ligated into λ DASH II replacement vector (Stratagene, Catalogue No. 247212) following the manufacturer's protocol. *E. coli* strains XL1-Blue MRA and XL1-blue MRA (P2) were utilized as host to titer the library. The library was subsequently amplified to a titer of $10^6$ plaques (based on XL1-Blue MRA (P2) host) per μl.

Approximately 40,000 plaques from the amplified library were plated out across 20 100 mm×15 mm petri plates. Duplicate plaque lifts were conducted after allowing the plates to chill at 4° C. for 5 hours. Plaque lifts were conducted by placing nylon membrane filters (S+S membrane, Midwest Scientific, Catalogue No. 77550) on the chilled petri plates for 10 min. The membranes were then placed, plaque side up, onto 3MM paper saturated with 0.2M NaOH/0.5M NaCl for 2 min. The filters were subsequently transferred, plaque side up, to 3MM paper saturated with 0.4M Tris-HCl (pH 7.6), 2× SSC for 2 min. The denatured recombinant phages were crosslinked by exposing the filters to 1200×100 μJOULES UV (Stratalinker® 2400). The filters were subsequently washed in 5× SSC prior to hybridization.

The filters were prehybridized in a solution containing 6× SSC, 5× Denhardt's, 100 μg/ml fish sperm DNA, and 0.1% SDS at 55° C. for approximately 2 hours. Filters were hybridized in the same medium as that for prehybridization utilizing the PHA synthase ORF from *A. eutrophus* (a gift from D. Dennis and C. Somerville) as a heterologous probe. The radiolabeled *A. eutrophus* PHA synthase ORF probe was prepared by random priming following the manufacturer's protocol (Prime-it II™ kit, Stratagene, Catalogue No. 300385) incorporating $dCT^{32}P$. Filters were hybridized for approximately 14 hours at 55° C. The filters were subsequently washed in 2× SSC and 0.1% SDS 2×, 15 min. each, at room temperature, followed by two additional washes in 1× SSC, 0.1% SDS at 55° C., prior to exposure to X-ray film for approximately 14 hours (Kodak imaging film, X-OMAT-AR, Catalogue No. 165-1512). Based on the duplicate lifts, 20 potential positive regions (each region contained 2–4 plaques) were isolated from the plates. Each of the 20 regions was placed in 1 ml of SM buffer (5.8 g/l NaCl, 2.0 g/l $MgSO_4 \cdot H_2O$, 50 ml of 1M Tris-HCl, pH 7.5, and 5.0 ml of 2% gelatin) with 20 μl chloroform, and placed at 4° C. for 5 hours. One μl of the SM buffer containing phage particles eluted from the isolated regions was used as inoculum for 200 μl of prepared host bacteria (XL1-Blue MRA (P2)). The secondary plaques were re-screened under the identical stringency described above. From the secondary screen, 18 positive plaques were selected for a tertiary screen to assure homogeneity. Following the tertiary screen, six positive plaques were carried on for phage DNA preparations.

Bacteriophage λ preparations were prepared following standard procedures (Sambrook et al., *Molecular Cloning A, Laboratory Manual*, Second Edition, 1989, Cold Spring Harbor Laboratory Press, Cold Spring Harbor, N.Y.). Aliquots of the DNA (approximately 1 μg) recovered from the six bacteriophage λ preparations were digested with the restriction enzymes Eco RI, HinD III, Not I, and Bgl II. All six preparations displayed the identical banding pattern following electrophoresis on a 0.8% agarose gel. Southern blot analysis of this gel, using as probe the radiolabeled PHA synthase ORF from *A. eutrophus* under the identical stringency used in the screening of the genomic library, was conducted. The purified PHA synthase ORF from A. eutrophus (approximately 10 ng) was included as a positive control. A single hybridizing band (Eco RI lane, approximate size of 21–23 kb) within each of the digested lanes was clearly visible following 1.5 hour exposure, although the intensity of the hybridizing fragment within the positive control lane was significantly greater than that observed within the digested bacteriophage preparations.

A single bacteriophage λ DNA preparation was subsequently digested with 15 single restriction enzymes and 12 double combinations of enzymes in order to localize the hybridizing fragment. The digests were electrophoresed on a 0.8% agarose gel along with the PHA synthase ORF of *A. eutrophus* as a positive control for the subsequent Southern blot analysis. The hybridizing fragment was localized to an approximately 6.5 kb Bam HI fragment, a 3.0 kb Sma I fragment, and a 10.0 kb Xho I fragment.

EXAMPLE 3

Sequencing of the *R. rubrum* PHA Synthase-
Encoding Fragment

Figure 3:
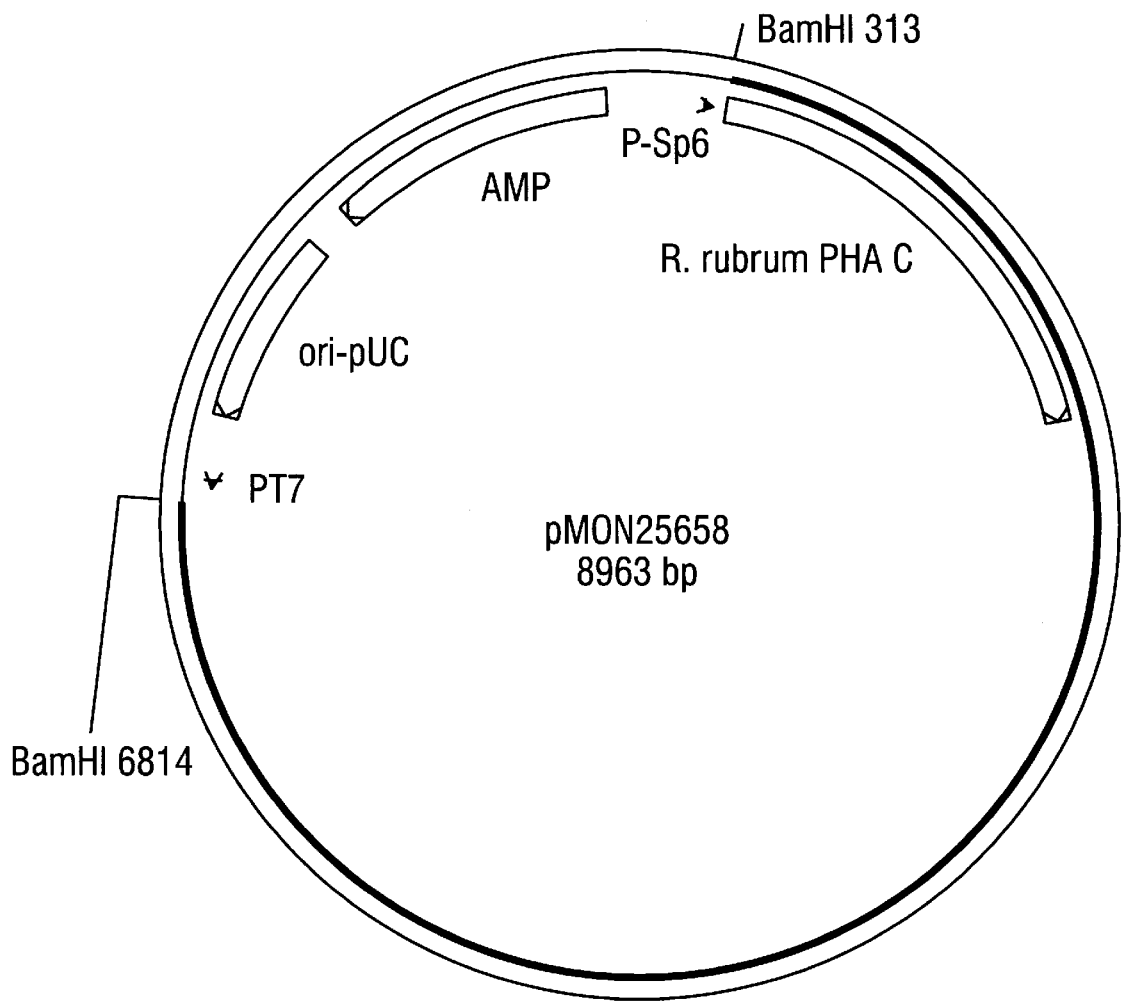
FIG. 3 is a map of pMON 25658. The solid black line represents the 6.5 kb Bam HI subclone containing the 5' region of the *R. rubrum* PHA synthase ORF. The open box corresponding to *R. rubrum* PHA C shows the coding region for the *R. rubrum* PHA synthase contained within this plasmid. PT7: promoter element for T7 RNA polymerase; P-Sp6: promoter element for Sp6 RNA polymerase.

The 3.0 kb Sma I and 6.5 kb Bam HI fragments were subcloned into the vector pSP72 (Promega, Catalogue No. P2191). The resultant plasmids are referred to as pMON 25657 and pMON 25658, respectively, and are schematically shown in FIGS. 2 and 3, respectively.

The DNA sequence of the 3.0 kb Sma I fragment within pMON 25657 was determined by double stranded sequence reactions utilizing a Prism™ DyeDeoxy Terminator Cycle Sequence Kit (Applied Biosystems, Catalogue No. 401434) or a Sequence™ Version 2.0 DNA Sequence Kit (USB, Catalgoue No. 70770). Double stranded reactions utilizing the former kit were analyzed on an Applied Biosystems 37 DNA sequencer, while the double stranded DNA sequence reactions performed with the latter kit were resolved by running the reaction products on an 8% acylamide gel and subsequently visualizing the sequence ladder by autoradiography. All reactions were conducted following manufacturers' protocols.

The entire PHA synthase ORF from *R. rubrum* (ATCC 25903) resided within the 3.0 kb Sma I fragment harbored in pMON 25657. The 3' end of the PHA synthase ORF was proximal to the sp6 primer. region within pSP72. A series of primers was designed to sequence both strands of the DNA that encode the PIA synthase from *R. rubrum*. The sequences of the coding and non-coding strands derived using these primers is shown in SEQ ID NO:1.

There are three putative translational initiation start sites in SEQ ID NO:1, i.e., at positions 8–10, 122–124, and 200–202, respectively. The corresponding amino acid sequences encoded thereby are shown in SEQ ID NOS:2–4, respectively. Most PHA synthases have a molecular weight in the range from 62–64 kD. Based on the predicted size (64 kD) of the deduced amino acid sequence shown in SEQ ID NO:3, and the location of a putative ribosomal binding site (GGGAGG) nine bases upstream of the ATG start codon at nucleotide positions 122–124 within SEQ ID NO:1, it is possible that the ATG at nucleotide positions 122–124 is the actual start site. There is also a purine-rich consensus-like sequence (GAGAAAAG) eight bases upstream of the ATG codon at nucleotide positions 200–202 as well.

EXAMPLE 4

Peptides, Polypeptides, and Proteins Biologically Functionally Equivalent To *R. rubrum* PHA Synthase The present invention includes not only the *R. rubrum* PHA synthase encoded by the nucleotide sequence shown in SEQ ID NO:1, but also biologically functional equivalent peptides, polypeptides, and proteins. The phrase "biologically functional equivalent peptides, polypeptides, and proteins" denotes peptides, polypeptides, and proteins that exhibit the same or similar PHA synthase enzymatic activity as the PHA synthase of *R. rubrum* when assayed biologically by. complementation utilizing the PHA-minus mutants of *Pseudomonas putida* (GpP104) (Huisman et al. (1991) *J. Biol. Chem.* 266:2191) or *Alcaligenes eutrophus* (DSM 541) Schlegel et al. (1970) *Arch. Microbiol.* 71:283), or enzymatically in vitro by monitoring the release of coenzyme A with DTNB (Valentin et al. (1994) *Appl. Microbiol. Biotechnol.* 40:699) or radiometrically (Gerngross et al. (1994) *Biochemistry* 33:9311). By "the same or similar PHA synthase enzymatic activity" is meant PHA synthase enzymatic activity differing from that of *R. rubrum* PHA synthase by about ±30% or less, preferably by about ±20% or less, more preferably by about ±10% or less, in such assays. These peptides, polypeptides, and proteins can contain a region or moiety exhibiting sequence similarity to a corresponding region or moiety of the *R. rubrum* PHA synthase disclosed herein, but this is not required as long as they exhibit the same or similar PHA synthase activity as that of the *R. rubrum* PHA synthase.

The *R. rubrum* PHA synthase is useful not only in the enzymatic synthesis of PHAs, but also as an antigen for the preparation of antibodies that can be used to purify or detect this PHA synthase.

Peptides, polypeptides, and proteins biologically functional equivalent to *R. rubrum* PHA synthase can occur in a variety of forms as described below.

Conservative Amino Acid Changes in the *R. rubrum* PHA Synthase Amino Acid Sequence Peptides, polypeptides, and proteins biologically functionally equivalent to *R. rubrum* PHA synthase include amino acid sequences containing conservative amino acid changes in the fundamental *R. rubrum* PHA sequence. In such amino acid sequences, one or more amino acids in the sequence is (are) substituted with another amino acid(s), the charge and polarity of which is (are) similar to that of the native amino acid, i.e., a conservative amino acid substitution, resulting in a silent change that does not significantly affect the PHA synthase enzymatic activity of the protein.

Substitutes for an amino acid within the fundamental *R. rubrum* PHA synthase amino acid sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid changes within the *R. rubrum* PHA synthase sequence can be made by substituting one amino acid within one of these groups with another amino acid within the same group. While biologically functional equivalents of *R. rubrum* PHA synthase can have any number of conservative amino acid changes that do not significantly affect the PHA synthase enzymatic activity of this enzyme, 10 or fewer conservative amino acid changes may be preferred. More preferably, seven or fewer conservative amino acid changes may be preferred; most preferably, five or fewer conservative amino acid changes may be preferred. The encoding nucleotide sequence (gene, cDNA, synthetic DNA, or mRNA) will thus have corresponding base substitutions, permitting it to code on expression for the biologically functional equivalent form of *R. rubrum* PHA synthase.

The biologically functional equivalent peptides, polypeptides, and proteins of *R. rubrum* PHA synthase encompassed by the present invention should generally possess at least about 70% sequence similarity, preferably at least about 80% sequence similarity, and most preferably at least about 90% sequence similarity to the naturally occurring protein, or corresponding region or moiety thereof. In this context, "sequence similarity" is determined by the "Gap" or "BestFit" programs of the Sequence Analysis Software Package, Genetics Computer Group, Inc., University of Wisconsin Biotechnology Center, Madison, Wis. 53711. This software matches similar sequences by assigning degrees of homology to various additions, deletions, substitutions, and other modifications. BestFit makes an optimal alignment of the best segment of similarity between two sequences. Optimal alignments are found by inserting gaps to maximize the number of matches using the local homology algorithm of Smith and Waterman (1981) *Adv. Appl. Math.* 2:482–489. Gap uses the algorithm of Needleman and Wunsch (1970 *J. Mol. Biol.* 48:443–453) to find the alignment of two complete sequences that maximizes the number of matches and minimizes the number of gaps.

Fragments and Variants of *R. rubrum* PHA Synthase

Fragments and variants of *R. rubrum* PHA synthase possessing the same or similar PHA synthase enzymatic activity as that of *R. rubrum* PHA synthase are also encompassed by the present invention.

Fragments of *R. rubrum* PHA Synthase

Fragments of *R. rubrum* PHA synthase can be truncated forms of the enzyme wherein one or more amino acids are deleted from the N-terminal end, C-terminal end, internal region of the protein, or combinations thereof, so long as such fragments retain the same or similar PHA synthase enzymatic activity as the naturally occurring *R. rubrum* PHA synthase. These fragments can be naturally occurring muteins of PHA synthase, or can be produced by restriction endonuclease treatment or Exonuclease III treatment (Henikoff (1984) *Gene* 28:351) of the encoding nucleotide sequence.

Variants of *R. rubrum* PHA Synthase

Variants of *R. rubrum* PHA synthase include forms of the enzyme wherein one or more amino acids in the naturally occurring amino acid sequence has(have) been substituted with another amino acid, or wherein one or more amino acids has (have) been inserted into the natural amino acid sequence. The variants contemplated herein retain the same or similar PHA synthase enzymatic activity as naturally occurring *R. rubrum* PHA synthase. These variants can be naturally occurring muteins of PHA synthase, or can be produced by random mutagenesis of the wild-type encoding nucleotide sequence (Greener et al. (1994) *Strategies* 7:32–34) or by replacing domains thereof with domains of other PHA synthases of interest. The PHA synthase activity of such variants can be assayed enzymatically or by complementation as described supra.

Combinations of the foregoing, i.e., forms of *R. rubrum* PHA synthase containing amino acid additions, deletions, and substitutions, but which retain the same or similar PHA synthase enzymatic activity as naturally occurring *R. rubrum* PHA synthase, are also encompassed by the present invention.

Fragments and variants of *R. rubrum* PHA synthase encompassed by the present invention should preferably possess at least about 70% sequence similarity, more preferably at least about 80% sequence similarity, and most preferably at least about 90% sequence similarity, to the natural *R. rubrum* PHA synthase or corresponding region or moiety thereof. Sequence similarity can be determined using the Gap or BestFit programs of the Sequence Analysis Software Packgage discussed above.

EXAMPLE 5

Nucleotide Sequences Biologically Functionally Equivalent to Genomic DNA Encoding *R. rubrum* PHA Synthase The present invention encompasses not only the *R. rubrum* genomic DNA sequence shown in SEQ ID NO:1, but also biologically functional equivalent nucleotide sequences. The phrase "biologically functional equivalent nucleotide sequences" denotes DNAs and RNAs. including genomic DNA, cDNA, synthetic DNA, and mRNA nucleotide sequences, that encode peptides, polypeptides, and proteins exhibiting the same or similar PHA synthase enzymatic activity as that of *R. rubrum* PHA synthase when assayed enzymatically or by complementation. Such biologically functional equivalent nucleotide sequences can encode peptides, polypeptides, and proteins that contain a region or moiety exhibiting sequence similarity to the corresponding region or moiety of the R. rubrum PHA synthase.

Nucleotide Sequences Encoding Conservative Amino Acid Changes in the *R. rubrum* PHA Synthase Amino Acid Sequence As noted in Example 4, supra, biologically functional equivalent nucleotide sequences of the present invention include nucleotide sequences that encode conservative amino acid changes within the *R. rubrum* PHA synthase amino acid sequence, producing silent changes therein. Such nucleotide sequences thus contain corresponding base substitutions based upon the genetic code compared to wild-type nucleotide sequences encoding *R. rubrum* PHA synthase.

Nucleotide Sequences Encoding Non-Conservative Amino Acid Substitutions, Additions, or Deletions in *R. rubrum* PHA Synthase In addition to nucleotide sequences encoding conservative amino acid changes within the naturally occurring *R. rubrum* PHA synthase amino acid sequence, biologically functional equivalent nucleotide sequences of the present invention also include genomic DNA, cDNA, synthetic DNA, and mRNA nucleotide sequences encoding non-conservative amino acid substitutions, additions, or deletions. These include nucleic acids that contain the same inherent genetic information as that contained in the genomic DNA of SEQ ID NO:1, and which encode peptides, polypeptides, or proteins exhibiting the same or similar PHA synthase enzymatic activity as that of *R. rubrum* PHA synthase. Such nucleotide sequences can encode fragments or variants of *R. rubrum* PHA synthase. The *R. rubrum* PHA synthase-like enzymatic activity of such fragments and variants can be identified by complementation or enzymatic assays as described above. These biologically functional equivalent nucleotide sequences can possess at least 70% sequence identity, preferably at least 80% sequence identity, and most preferably at least 90% sequence identity, to naturally occurring *R. rubrum* PHA synthase genomic DNA, cDNA, synthetic DNA, and mRNA, respectively, or corresponding regions or moieties thereof.

Mutations made in *R. rubrum* PHA synthase cDNA, genomic DNA, synthetic DNA, mRNA, or other nucleic acid preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, site-directed mutagenesis can be conducted at the target codon (Thompson et al. (1988) *Biochemistry* 28:57335), and the PHA synthase enzymatic activity of the resulting peptide, polypeptide, or protein can be determined enzymatically or by complementation.

In the present invention, nucleic acids biologically functionally equivalent to *R. rubrum* PHA synthase genomic DNA having the nucleotide sequence shown in SEQ ID NO:1 include:

(1) DNAs originating from R. rubrum, exemplified herein by *R. rubrum* ATCC 25903, the length of which has been altered either by natural or artificial mutations such as partial nucleotide insertion or deletion, or the like, so that when the entire length of the coding sequence within SEQ ID NO:1 is taken as 100%, the biologically functional equivalent nucleotide sequence has an approximate length of about 60–120% thereof, preferably about 80–110% thereof; or (2) nucleotide sequences containing partial (usually 20% or less, preferably 10% or less, more preferably 5% or less of the entire length) natural or artificial mutations so that such sequences code for different amino acids, but wherein the resulting protein retains the same or similar PHA synthase enzymatic activity as that of naturally occurring *R. rubrum* PHA synthase. The mutated DNAs created in this manner should preferably encode a protein having at least about 70%, preferably at least about 80%, and more preferably at least about 90%, sequence similarity to the amino acid sequence of the *R. rubrum* PHA synthase. Sequence similarity can be assessed by the Gap or BestFit programs of the Sequence Analysis Software Package discussed above.

The methods that can be employed to create the artificial nucleic acid mutations contemplated herein are not specifically limited, and can be produced by any of the means conventional in the art. For example, the *R. rubrum* PHA synthase gene, cDNA, or synthetic DNA can be treated with appropriate restriction enzymes so as to insert or delete desired DNA fragments so that the proper nucleic acid reading frame is preserved. Subsequent to restriction endonuclease treatment, the digested DNA can be treated to fill in any overhangs, and the DNA religated. C-terminal deletions can be produced by Exonuclease III treatment of the DNA. Alternatively, various domains of the *R. rubrum* PHA synthase can be replaced with regions of other PHA synthases by appropriate nucleic acid manipulations employing restriction enzymes, followed by ligation.

Mutations can also be introduced at particular loci by synthesizing oligonucleotides containing a mutant sequence flanked by restriction sites enabling ligation to fragments of the native *R. rubrum* PHA synthase genomic DNA, cDNA, or synthetic DNA sequence. Following ligation, the resulting reconstructed sequence encodes a biologically functional equivalent having the desired amino acid insertion, substitution, or deletion.

Alternatively, oligonucleotide-directed site-specific or segment-specific mutagenesis procedures can be employed to produce an altered DNA sequence having particular codons altered according to the insertion, substitution, or deletion required.

Exemplary methods of making the alterations described above are disclosed by Walder et al. (1986) *Gene* 42:133; Bauer et al. (1985) *Gene* 37:73; Craik (January, 1985) *BioTechniques*, pp. 12–19; Smith et al. (1981) *Genetic Engineering: Principles and Methods*, Plenum Press; Ausubel et al. (1989) *Current Protocols in Molecular Biology*, John Wiley & Sons, Inc.; Sambrook et al. (1989) *Molecular Cloning: A Laboratory Manual*, Second Edition, Cold Spring Harbor Laboratory Press, Cold Spring Harbor, N.Y.; Frits Eckstein et al. (1982) *Nucleic Acids Research* 10:6487–6497, and Osuna et al. (1994) *Critical Reviews In Microbiology*, 20:107–116.

Biologically functional equivalents to the genomic DNA sequence disclosed herein produced by any of the foregoing methods can be selected for by complementation or enzymatic assay of the resulting peptides, polypeptides, or proteins as described above.

Alternatively, mutations can be introduced at particular loci by synthesizing oligonucleotides containing a mutant sequence flanked by restriction sites facilitating ligation to fragments of the native *R. rubrum* PHA synthase nucleotide sequence. Following ligation, the resulting reconstructed nucleotide sequence encodes a biologically functional equivalent form of synthase having the desired amino acid insertion, substitution, or deletion. The mutant forms so produced can be screened for *R. rubrum*-like PHA synthase activity by complementation or enzymatic assays.

Useful biologically functional equivalent forms of the genomic DNA of SEQ ID NO:1 include DNAs comprising nucleotide sequences that exhibit a level of sequence identity to corresponding regions or moieties of the genomic DNA of SEQ ID NO:1 of at least about 70%, preferably at least about 80%, and more preferably at least about 90%. Sequence identity can be determined using the BestFit or Gap programs discussed above.

Genetically Degenerate Nucleotide Sequences

Due to the degeneracy of the genetic code, i.e., the existence of more than one codon for most of the amino acids naturally occurring in proteins, genetically degenerate DNA (and RNA) sequences that contain the same essential genetic information as the genomic DNA of the present invention, and which encode the same amino acid sequence as that of *R. rubrum* PHA synthase, are encompassed by the present invention. Genetically degenerate forms of any of the other nucleic acid sequences discussed herein are encompassed by the present invention as well.

Biologically Functional Equivalent Nucleic Acid Sequences Detected by Hybridization Although one embodiment of a nucleotide sequence encoding *R. rubrum* PHA synthase is shown in SEQ ID NO:1, it should be understood that other biologically functional equivalent forms of R. rubrum PHA synthase-encoding nucleic acids can be readily isolated using conventional DNA-DNA or DNA-RNA hybridization techniques. Thus, the present invention also includes nucleotide sequences that hybridize to SEQ ID NO:1 and its complementary sequence, and that code on expression for peptides, polypeptides, and proteins exhibiting the same or similar enzymatic activity as that of R. rubrum PHA synthase. Such nucleotide sequences preferably hybridize to SEQ ID NO:1 or its complementary sequence under moderate to high stringency (see Sambrook et al. (1989) Molecular Cloning: A Laboratory Manual, Second Edition, Cold Spring Harbor Laboratory Press, Cold Spring Harbor, N.Y.). Exemplary conditions include initial hybridization in 6× SSC, 5× Denhardt's solution, 100 µg/ml fish sperm DNA, 0.1% SDS, at 55° C. for sufficient time to permit hybridization (e.g., several hours to overnight), followed by washing two times for 15 min. each in 2× SSC, 0.1% SDS, at room temperature, and two times for 15 min. each in 0.5–1× SSC, 0.1% SDS, at 55° C., followed by autoradiography. Typically, the nucleic acid molecule is capable of hybridizing when the hybridization mixture is washed at least one time in 0.1× SSC at 55° C., preferably at 60° C., and more preferably at 65° C.

The present invention also encompasses nucleotide sequences that hybridize to genomic DNA, cDNA, or synthetic DNA molecules that encode the amino acid sequence of R. rubrum PHA synthase, or genetically degenerate forms thereof due to the degeneracy of the genetic code, under salt and temperature conditions equivalent to those described supra, and that code on expression for a peptide, polypeptide, or protein that has the same or similar PHA synthase enzymatic activity as that of R. rubrum PHA synthase.

The nucleotide sequences described above are considered to possess a biological function substantially equivalent to that of the R. rubrum PHA synthase gene of the present invention if they encode peptides, polypeptides, or proteins having PHA synthase enzymatic activity differing from that of R. rubrum PHA synthase by about ±30% or less, preferably by about ±20% or less, and more preferably by about ±10% or less when assayed in vivo by complementation or by the enzymatic assays discussed above.

Biologically Functional Equivalent Nucleic Acid Sequences Detected by Complementation An E. coli donor strain harboring a broad host range plasmid comprising a putative biologically functional equivalent nucleic acid in cis with all regulatory elements necessary for expression can be used to conjugate the plasmid into a recipient PHA-minus bacterial strain by triparental mating using the helper plasmid pRK2013 (Ditta et al. (1980) Proc. Natl. Acad. Sci. USA 77:7347). Resulting transconjugants can be selected on polymer-conducive medium supplemented with appropriate antibiotics. Fermentation of the transconjugants in media containing different carbon substrates and subsequent analysis of the resulting PHA provides a means of determining the functional equivalency of the nucleic acid.

Genomic Probes

In another aspect, the present invention provides oligonucleotide hybridization probes useful in screening genomic and other nucleic acid libraries for DNA sequences encoding peptides, polypeptides, or proteins having enzymatic activity the same or similar to that of R. rubrum PHA synthase, which probes can be designed based on the sequences provided in SEQ IDS NO:1–4. Especially useful probes, including degenerate probes, can be designed based on those regions that are highly conserved, or that show a high level of sequence similarity, among PHA synthases. Such probes can range from about 20 to about 60 nucleotides in length, generally about 20 nucleotides in length, more typically about 30 nucleotides in length, preferably about 40 nucleotides in length, and more preferably about 50–60 nucleotides in length. Preferably, these probes specifically hybridize to R. rubrum genomic DNA and other DNA sequences encoding peptides, polypeptides, or proteins having the same or similar PHA synthase enzymatic activity as that of R. rubrum PHA synthase under hybridization conditions such as those described above. Such oligonucleotide probes can be synthesized by automated synthesis, and can be conveniently labeled at the 5' end with a reporter molecule such as a radionuclide, e.g., $^{32}p$, or biotin. The library to be probed can be plated as colonies or phage, depending upon the vector employed, and the recombinant DNA transferred to nylon or nitrocellulose membranes. Following denaturation, neutralization, and fixation of the DNA to the membrane, the membrane is hybridized fith the labeled probe. Following this, the membrane is washed, and the reporter molecule detected. Colonies or phage harboring hybridizing DNA are then isolated and propagated. Candidate clones or PCR-amplified fragments can be verified as comprising DNA encoding R. rubrum-like PHA synthase activity or related peptides, polypeptides, or proteins having enzymatic activity the same as or similar to R. rubrum PHA synthase by a variety of methods. For example, the candidate clones can be hybridized with a second, non-overlapping probe, or subjected to DNA sequence analysis. The enzymatic activity of the peptide, polypeptide, or protein encoded thereby can be assessed by cloning and expression of the DNA in an appropriate host such as E. coli, followed by isolation of the peptide, polypeptide, or protein and assay of the enzymatic activity thereof. By such means, nucleic acids encoding PHA synthases from microorganisms other than R. rubrum, as well as peptides, polypeptides, and proteins biologically functionally equivalent to R. rubrum PHA synthase, useful in producing PHAs, can be isolated.

Degenerate Oligonucleotide Primers

Biologically functional equivalent PHA synthase genes from other microorganisms, or equivalent PHA synthase-encoding cDNAs or synthetic DNAs, can also be isolated by amplification using Polymerase Chain Reaction (PCR) methods. Degenerate oligonucleotide primers based on the amino acid sequence of R. rubrum PHA synthase can be prepared and used in conjunction with PCR technology employing reverse transcriptase (E. S. Kawasaki (1990), In Innis et al., Eds., PCR Protocols, Academic Press, San Diego, Chapter 3, p. 21) to amplify biologically functional equivalent DNAs from genomic or cDNA libraries of other organisms.

Alternatively, the degenerate oligonucleotides can be used as probes to screen cDNA libraries in, for example, λ phage vectors such as λ Zap.II (Stratagene).

EXAMPLE 6

Production of Polyhydroxyalkanoates in Bacteria and Plants Expressing the R. rubrum PHA Synthase The PHA synthase-encoding DNA of R. rubrum can be introduced into and expressed in a variety of different bacterial and plant host cells to facilitate the production of PHAs therein. It should be understood that reference to the *R. rubrum* PHA synthase and genomic DNA encoding the same in this context includes the biologically functional equivalents thereof, respectively, discussed above. The advantages of this approach to the production of PHAs include decreasing the dependence on petroleum-derived monomers, and the ease with which bacteria and plants can be grown on a large scale.

PHA synthesis in bacteria and plants requires at least three genes: β-ketothiolase (pha A), acetoacetyl-CoA reductase (phaB), and PHA synthase (phbC). Methods for incorporating these genes into transformation/expression vector constructs and introducing these constructs into bacterial and plant host cells to produce PHAs in such cells are well known in the art. Poirier et al. ((1995) *Bio/Technology* 13:142–150) have recently provided an extensive review of progess in this area. In general, such vector constructs comprise assemblies of DNA fragments operatively linked in a functional manner such that they drive the expression of the structural DNA sequences contained therein. These vector constructs usually contain a promoter that functions in the selected host cell, along with any other necessary regulatory regions such as ribosome binding sites, transcription terminators, 3' non-translated polyadenylation signals, etc., linked together in an operable manner, as well as selectable markers (Sambrook et al., *Molecular Cloning: A Laboratory Manual*, Second Edition, 1989, Cold Spring Harbor Laboratory Press, Cold Spring Harbor, N.Y.; Ausubel et al. (1989) *Current Protocols in Molecular Biology*, John Wiley & Sons, Inc.).

Such vectors can be introduced into bacterial cells by calcium chloride/heat shock treatment or electroporation. Transformed host cells can subsequently be selected for on selective media, cultured in an appropriate medium for a time and under conditions conducive to the production of PHA, and the PHA can then be recovered. Representative methods have been described by Slater et al. (1988) *J. Bacteriol.* 170:4431–4436; Slater et al. (1992) *Appl. Environ. Microbiol.* 58:1089–1094; Zhang et al. (1994) *Appl. Environ. Microbiol.* 60:1198–1205; and Kidwell et al. (1995) *Appl. Environ. Microbiol.* 61:1391–1398.

Particularly useful host bacteria for PHA polymer production employing the *R. rubrum* PHA synthase include Alcaligenes (e.g., *A. eutrophus*), *Escherichia coli*, Klebsiella (e.g., *K aerogenes* and *K oxytoca*), Nocardia (e.g., *N. corallina*), and Pseudomonas (e.g., *P. putida*).

In plants, transformation vectors capable of introducing bacterial genes involved in PHA biosynthesis are easily designed. Generally, such vectors comprise one or more coding sequences of interest under the transcriptional control of 5' and 3' regulatory sequences, including a promoter, and a selectable marker. Typical regulatory sequences include a transcription initiation start site, a ribosome binding site, an RNA processing signal, a transcription termination site, and/or a polyadenylation signal. Plant promoter sequences can be inducible or constitutive, environmentally- or developmentally-regulated, or cell- or tissue-specific. Often-used promoters include the CAMV 35S promoter, the enhanced CAMV 35S promoter, the nopaline synthase promoter, and the octopine synthase promoter. Representative vectors often comprise, operatively. linked in sequence in the 5' to 3' direction, a promoter sequence that directs the transcription of a downstream heterologous structural DNA in a plant; optionally, a non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein.

A variety of different methods can be employed to introduce such vectors into plant protoplasts, cells, callus tissue, leaf discs, meristems, etc., to generate transgenic plants, including Agrobacterium-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol.* 42:205–225). In general, transgenic plants comprising cells containing and expressing *R. rubrum* PHA synthase-encoding DNA can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the *R. rubrum* PHA synthase-encoding nucleotide sequence.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the entire pathway into a single plant. Successful production of the PHA polyhydroxybutyrate in cells of Arabidopsis has been demonstrated by Poirier et al. (1992) *Science* 256:520–523, and in plastids thereof by Nawrath et al. (1994) *Proc. Natl. Acad. Sci. USA* 91:12760–12764.

Specific methods for transforming a wide variety of dicots and obtaining transgenic plants are well documented in the literature (see Gasser and Fraley (1989) *Science* 244:1293; Fisk and Dandekar (1993) *Scientia Horticulturae* 55:5–36; Christou (1994) *Agro Food Industry Hi Tech* (March/April 1994) p.17, and the references cited therein).

Successful transformation and plant regeneration have been achieved in the monocots as follows: asparagus (*Asparagus officinalis*; Bytebier et al. (1987) *Proc. Natl. Acad. Sci. USA* 84:5345 ); barley (*Hordeum vulgarae*; Wan and Lemaux (1994) *Plant Physiol.* 104:37); maize (*Zea mays*; Rhodes et al. (1988) *Science* 240:204; Gordon-Kamm et al. (1990) *Plant Cell* 2:603; Fromm et al. (1990) *Bio/Technology* 8:833; Koziel et al. (1993) *Bio/Technology* 11:194); oats (*Avena sativa*; Somers et al. (1992) *Bio/Technology* 10:1589); orchardgrass (*Dactylis glomerata*; Horn et al. (1988) *Plant Cell Rep.* 7:469); rice (*Oryza sativa*, including indica and japonica varieties; Toriyama et al. (1988) *Bio/Technology* 6:10; Zhang et al. (1988) *Plant Cell Rep.* 7:379; Luo and Wu (1988) *Plant Mol. Biol. Rep.* 6:165; Zhang and Wu (1988) *Theor. Appl. Genet.* 76:835; Christou et al. (1991) *Bio /Technology* 9:957); rye (*Secale cereale*; De la Pena et al. (1987) *Nature* 325:274); sorghum (*Sorghum bicolor*; Cassas et al. (1993) *Proc. Natl. Acad. Sci. USA* 90:11212); sugar cane (*Saccharum spp.*; Bower and Birch (1992) *Plant J.* 2:409); tall fescue (*Festuca arundinacea; Wang et al. (1992) Bio/Technology* 10:691); turfgrass (*Agrostis palustris*; Zhong et al. (1993) *Plant Cell Rep.* 13:1); and wheat (*Triticum aestivum*; Vasil et al. (1992) *Bio /Technology* 10:667; Troy Weeks et al. (1993) *Plant Physiol.* 102:1077; Becker et al. (1994) *Plant J.* 5:299).

Particularly useful plants for PHA polymer production include those, such as potato and sugarbeet, that produce carbon substrates which can be employed for PHA biosynthesis. Cereal plants such as corn, wheat, and rice are also preferred. Other useful plants include tobacco and high oil seed plants such as soybean, canola, oil seed rape, and peanut. Plants that grow in desert or in mineralized soil are also preferred. Polymers that can be produced in this manner include PHB, and copolymers incorporating both short chain length and medium chain length monomers, such as PHB-co-PHV.

If the host plant of choice does not produce the requisite fatty acid substrates, appropriate β-ketothiolase and reductase genes can be introduced therein along with the *R. rubrum* PHA synthase. Host plants can also be modified, for example by mutagenesis, to block the glycerol ester and fatty acid degradation pathways so that they accumulate the appropriate substrates for PHA production.

The invention being thus described, it will be obvious that the same can be varied in many ways. Such variations are not to be regarded as a departure from the spirit and scope of the present invention, and all such modifications as would be obvious to one skilled in the art are intended to be included within the scope of the following claims.

What is claimed is:

1. An isolated DNA molecule, comprising a nucleotide sequence elected from the group consisting of:

(a) the nucleotide sequence of the coding strand shown in SEQ ID NO:1, or the complement thereof;

(b) a nucleotide sequence that hybridizes to said nucleotide sequence of (a) under a wash stringency equivalent to 0.5× SSC to 2× SSC, 0.1% SDS, at 55°–65° C., and which encodes an enzyme having *Rhodospirillum rubrum* poly-β-hydroxyalkanoate synthase enzymatic activity;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

2. The isolated DNA molecule of claim 1, wherein said wash stringency is equivalent to 2× SSC, 0.1% SDS, at 55° C.

3. The isolated DNA molecule of claim 1, wherein said wash stringency is equivalent to 1× SSC, 0.1% SDS, at 55° C.

4. The isolated DNA molecule of claim 1, wherein said wash stringency is equivalent to 0.5× SSC, 0.1% SDS, at 55° C.

5. An isolated DNA molecule, comprising the nucleotide sequence shown in SEQ ID NO:1.

6. A transformation vector comprising a DNA molecule according to claim 1.

7. A host cell containing a transformation vector according to claim 6.

8. The host cell of claim 7, which is a bacterial cell.

9. The host cell of claim 7, which is a plant cell.

10. A transgenic plant comprising plant cells according to claim 9.

* * * * *